US008257705B2

(12) United States Patent
Tanha et al.

(10) Patent No.: US 8,257,705 B2
(45) Date of Patent: Sep. 4, 2012

(54) SINGLE-DOMAIN ANTIGEN-BINDING ANTIBODY FRAGMENTS DERIVED FROM LLAMA ANTIBODIES

(75) Inventors: Jamshid Tanha, Ottawa (CA); Ginette Dubuc, Ottawa (CA); Saran Narang, Ottawa (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 11/477,830

(22) Filed: Jun. 29, 2006

(65) Prior Publication Data

US 2006/0246058 A1   Nov. 2, 2006
US 2008/0124324 A9   May 29, 2008

Related U.S. Application Data

(62) Division of application No. 10/031,874, filed as application No. PCT/CA01/00763 on May 25, 2001, now abandoned.

(60) Provisional application No. 60/207,234, filed on May 26, 2000.

(51) Int. Cl.
*A61K 39/395* (2006.01)
*C07K 16/44* (2006.01)
*C40B 40/08* (2006.01)
*C40B 40/10* (2006.01)

(52) U.S. Cl. .................................. 424/133.1; 530/387.3
(58) Field of Classification Search ................ 424/133.1; 530/387.3
See application file for complete search history.

(56) References Cited

U.S. PATENT DOCUMENTS

| | | | |
|---|---|---|---|
| 5,182,107 | A | 1/1993 | Friden |
| 5,759,808 | A | 6/1998 | Casterman et al. |
| 5,792,457 | A | 8/1998 | Tuomanen et al. |
| 5,800,988 | A | 9/1998 | Casterman et al. |
| 5,840,526 | A | 11/1998 | Casterman et al. |
| 5,855,885 | A | 1/1999 | Smith et al. |
| 5,874,541 | A | 2/1999 | Casterman et al. |
| 6,172,197 | B1 | 1/2001 | McCafferty et al. |
| 6,399,763 | B1 | 6/2002 | Frenken et al. |

FOREIGN PATENT DOCUMENTS

| | | |
|---|---|---|
| EP | 0 739 981 A | 10/1996 |
| EP | 0 934 953 A | 8/1999 |
| WO | WO 94/04678 A1 | 3/1994 |
| WO | WO 99/37681 A2 | 7/1999 |
| WO | WO 99/42077 A | 8/1999 |
| WO | WO 00/43507 A | 7/2000 |

OTHER PUBLICATIONS

Nguyen et al. J. Mol. Biol., 275:413-418, 1998.*
Ibragimova and Eade (Biophysical Journal, Oct 1999, vol. 77, pp. 2191-2198).*
Davies, J. et al., "Antibody VH domains as small recognition units," *Bio/Technology*, 13: 475-479 (1995).
Ghahroudi, A., "Selection and identification of single domain antibody fragments from camel heavy-chain antibodies," *FEBS Letters*, 414: 521-526 (1997).
Hoogenboom, H. et al., "Antibody phage display technology and its applications," *Immunotechnology*, 4: 1-20 (1998).
Krebber, C. et al., "Co-selection of cognate antibody-antigen pairs by selectively-infective phages," *FEBS*, 337: 227-231 (1995).
Lauwereys, M. et al., "Potent enzyme inhibitors derived from dromedary heavy-chain antibodies," *The Embo Journal*, 17: 3512-3520 (1998).
Nguyen, V. et al., "Camel-heavy chain antibodies: diverse germline VHH and specific mechanisms enlarge the antigen-binding repertoire," *The Embo Journal*, 19: 921-930 (2000).
Sampath, A. et al., "Versatile vectors for direct cloning and ligation-independent cloning of PCT-amplified fragments for surface display on filamentous bacteriophages," *Gene*, 190: 5-10 (1997).
Blier et al., "A Limited Number of B Cell Lineages Generates the Heterogeneity of a Secondary Immune Response," *The Journal of Immunology*, vol. 139, 3996-4006, No. 12, Dec. 15, 1987.
Cai et al., "A melanoma-specific $V_H$ antibody cloned from a fusion phage library of a vaccinated melanoma patient," *Proc. Natl. Acad. Sci. USA*, vol. 93, 6280-6285, Jun. 1996.
Crews et al., "A Single $V_H$ Gene Segment Encodes the Immune Response to Phosphorylcholine: Somatic Mutation Is Correlated with the Class of the Antibody," *Cell*, vol. 25, 59-66, Jul. 1981.
Davies et al., "'Camelising' human antibody fragments: NMR studies on VH domains," *FEBS Letters* 339 (1994) 285-290.
Decanniere et al., "A single-domain antibody fragment in complex with RNase A: non-canonical loop structures and nanomolar affinity using two CDR loops," *Structure*, 1999, vol. 7, No. 4, 361-370.
Ghahroudi et al., "Selection and identification of single domain antibody fragments from camel heavy-chain antibodies," *FEBS Letters* 414 (1997) 521-526.
Desmyter et al., "Crystal structure of a camel single-domain $V_H$ antibody fragment in complex with lysozyme," *Nature Structural Biology*, vol. 3, No. 9, Sep. 1996, 803-811.

(Continued)

*Primary Examiner* — Lynn Bristol
(74) *Attorney, Agent, or Firm* — Wolf, Greenfield & Sacks, P.C.

(57) ABSTRACT

A phage display library of variable heavy domain ($V_HH$ or VH) fragments (sdAb fragments) derived from the antibody repertoire of a non-immunized llama is disclosed. The sdAb fragments of the library are characterized by the absence of cysteine residues in complementarity determining regions (CDRs) and a very low presence of residues of glutamic acid, arginine and glycine at positions 44, 45 and 47, respectively, of the VL interface of the variable heavy domain $V_HH$. The large size of the library (in the order of $10^9$) makes it a source of antigen-binding fragments having high affinity to almost any antigen of interest. The library is preferably generated using a modified fd-tet phage growing in plaques in the absence of a tetracycline.

17 Claims, 7 Drawing Sheets

OTHER PUBLICATIONS

Hamers-Casterman et al., "Naturally occurring antibodies devoid of light chains," *Nature*, vol. 363, 446-448, Jun. 3, 1993.

Muyldermans et al., "Sequence and structure of $V_H$ domain from naturally occurring camel heavy chain immunoglobulins lacking light chains," *Protein Engineering*, vol. 7, No. 9, 1129-1135, 1994.

Tomlinson et al., "The Repertoire of Human Germline $V_H$ Sequences Reveals about Fifty Groups of $V_H$ Segments with Different Hypervariable Loops," *J. Mol. Biol.* (1992) 227, 776-798.

Vu et al., "Comparison of Llama $V_H$ Sequences from Conventional and Heavy Chain Antibodies," *Molecular Immunology*, vol. 34, No. 16-17, pp. 1121-1131, 1997.

Ward et al., "Binding activities of a repertoire of single immunoglobulin variable domains secreted from *Escherichia coli*," *Nature*, vol. 341, Oct. 12, 1989, 544-546.

Davies, J. et al., "Single antibody domains as small recognition units: design and in vitro antigen selection of camelized, human VH domains with improved protein stability," *Protein Engineering* 1996; 9(6):531-537.

Dübel, Stefan (Editor); *Handbook of Therapeutic Antibodies*; vol. 1: Technologies; ISBN: 978-3-527-31453-9; Jan. 2007; pp. 97-98.

Fan, Z. et al., "Three-dimensional Structure of an Fv from a Human IgM Immunoglobulin," *J. Mol. Biol.* 1992; 228:188-207.

Muyldermans, S., "Single domain camel antibodies: current status," *Reviews in Molecular Biotechnology* 2001; 74:277-302.

Reiter, Y. et al., "An Antibody Single-domain Phage Display Library of a Native Heavy Chain Variable Region: Isolation of Functional Single-domain VH Molecules with a Unique Interface," *J. Mol. Biol.* 1999; 290:685-698.

Abbas, A.K. et al., *Cellular and Molecular Immunology* 3$^{rd}$ ed., Pub. by W.B. Saunders Company; 1997, pp. 38 and 58 only.

Abhinandan, K.R. et al., "Analysis and improvements to Kabat and structurally correct numbering of antibody variable domains," *Molecular Immunology* 2008; 45:3832-3839.

Li, J.Y. et al., "Genetically engineered brain drug delivery vectors: cloning, expression and in vivo application of an anti-transferrin receptor single chain antibody-streptavidin fusion gene and protein," *Protein Engineering* 1999; 12(9):787-796.

Morrison, S.L. et al., "Genetically engineered antibodies and their application to brain delivery," *Advanced Drug Delivery Reviews* 1995; 15:147-175.

Stanimirovic, D. et al., "Angiotensin II-Induced Fluid Phase Endocytosis in Human Cerebromicrovascular Endothelial Cells Is Regulated by the Inositol-Phosphate Signaling Pathway," *Journal of Cellular Physiology* 1996; 169:455-467.

Sternberger, N.H. et al., "Blood-brain barrier protein recognized by monoclonal antibody," *Proc. Natl. Acad. Sci. USA* 1987; 84:8169-8173.

Riechmann et al., "Single domain antibodies: comparison of camel VH and camelised human VH domains," *Journal of Immunological Methods* 1999; 231:25-38.

Tanha, J. et al., "Improving solubility and refolding efficiency of human $V_H$s by a novel mutational approach," *Protein Engineering, Design & Selection* 2006; 19(11):503-509.

Tanha, J. et al., "Selection by phage display of llama conventional $V_H$ fragments with heavy chain antibody $V_H$H properties," *Journal of Immunological Methods* 2002; 263:97-109.

Vranken, W. et al., "Solution Structure of a Llama Single-Domain Antibody with Hydrophobic Residues Typical of the VH/VL Interface," *Biochemistry* 2002; 41:8570-8576.

* cited by examiner

SEQUENCE LISTING

<160> NUMBER OF SEQ ID NOS: 212

<210> SEQ ID NO 1
<211> LENGTH: 10
<212> TYPE: PRT
<213> ORGANISM: Lama glama

<400> SEQUENCE: 1

Gly Phe Thr Phe Ser Ser Tyr Tyr Met Ser
 1               5                   10

<210> SEQ ID NO 2
<211> LENGTH: 10
<212> TYPE: PRT
<213> ORGANISM: Lama glama

<400> SEQUENCE: 2

-continued

Gly Arg Thr Phe Ser Asn Tyr His Met Gly
 1               5                   10

<210> SEQ ID NO 3
<211> LENGTH: 10
<212> TYPE: PRT
<213> ORGANISM: Lama glama

<400> SEQUENCE: 3

Gly Arg Ile Phe Ser Asn Ala Ala Met Gly
 1               5                   10

<210> SEQ ID NO 4
<211> LENGTH: 10
<212> TYPE: PRT
<213> ORGANISM: Lama glama

<400> SEQUENCE: 4

Arg Ser Ile Phe Ser Ile Asn Thr Leu Gly
 1               5                   10

<210> SEQ ID NO 5
<211> LENGTH: 10
<212> TYPE: PRT
<213> ORGANISM: Lama glama

<400> SEQUENCE: 5

Gly Arg Ser Phe Ser Thr Tyr Arg Val Gly
 1               5                   10

<210> SEQ ID NO 6
<211> LENGTH: 10
<212> TYPE: PRT
<213> ORGANISM: Lama glama

<400> SEQUENCE: 6

Gly Asn Thr Ile Ser Gly Tyr Ala Thr Gly
 1               5                   10

<210> SEQ ID NO 7
<211> LENGTH: 10
<212> TYPE: PRT
<213> ORGANISM: Lama glama

<400> SEQUENCE: 7

Gly Gly Ser Phe Ser Asn Tyr Asn Met Gly
 1               5                   10

<210> SEQ ID NO 8
<211> LENGTH: 10
<212> TYPE: PRT
<213> ORGANISM: Lama glama

<400> SEQUENCE: 8

Gly Arg Ile Pro Arg Asn Tyr Pro Ile Gly
 1               5                   10

<210> SEQ ID NO 9
<211> LENGTH: 10
<212> TYPE: PRT
<213> ORGANISM: Lama glama

<400> SEQUENCE: 9

Gly Glu Ser Ile Ala Ser Phe Asn Leu Gly
 1               5                   10

```
<210> SEQ ID NO 10
<211> LENGTH: 10
<212> TYPE: PRT
<213> ORGANISM: Lama glama

<400> SEQUENCE: 10

Gly Arg Thr Phe Ser Ser Val Ser Met Gly
 1               5                  10

<210> SEQ ID NO 11
<211> LENGTH: 10
<212> TYPE: PRT
<213> ORGANISM: Lama glama

<400> SEQUENCE: 11

Gly Leu Thr Phe Gly Asp Tyr Ala Met Gly
 1               5                  10

<210> SEQ ID NO 12
<211> LENGTH: 10
<212> TYPE: PRT
<213> ORGANISM: Lama glama

<400> SEQUENCE: 12

Gly Arg Thr Phe Ser Ser Val Thr Met Gly
 1               5                  10

<210> SEQ ID NO 13
<211> LENGTH: 10
<212> TYPE: PRT
<213> ORGANISM: Lama glama

<400> SEQUENCE: 13

Gly Arg Thr Phe Ser Arg Phe Ala Met Gly
 1               5                  10

<210> SEQ ID NO 14
<211> LENGTH: 10
<212> TYPE: PRT
<213> ORGANISM: Lama glama

<400> SEQUENCE: 14

Gly Ser Ile Phe Ser Glu Ser Ala Met Gly
 1               5                  10

<210> SEQ ID NO 15
<211> LENGTH: 10
<212> TYPE: PRT
<213> ORGANISM: Lama glama

<400> SEQUENCE: 15

Gly Arg Thr Phe Ser Ser Asp Ala Met Gly
 1               5                  10

<210> SEQ ID NO 16
<211> LENGTH: 10
<212> TYPE: PRT
<213> ORGANISM: Lama glama

<400> SEQUENCE: 16

Gly Phe Thr Phe Ser Asn Phe Trp Met Gly
 1               5                  10

<210> SEQ ID NO 17
```

```
<211> LENGTH: 10
<212> TYPE: PRT
<213> ORGANISM: Lama glama

<400> SEQUENCE: 17

Gly Arg Ser Phe Asn His Tyr Ile Met Gly
1               5                   10

<210> SEQ ID NO 18
<211> LENGTH: 10
<212> TYPE: PRT
<213> ORGANISM: Lama glama

<400> SEQUENCE: 18

Gly Leu Pro Phe Ser Thr Tyr Ser Met Gly
1               5                   10

<210> SEQ ID NO 19
<211> LENGTH: 10
<212> TYPE: PRT
<213> ORGANISM: Lama glama

<400> SEQUENCE: 19

Gly Arg Thr Phe Ser Thr Tyr Thr Met Gly
1               5                   10

<210> SEQ ID NO 20
<211> LENGTH: 10
<212> TYPE: PRT
<213> ORGANISM: Lama glama

<400> SEQUENCE: 20

Gly Tyr Thr Phe Ser Ser His Ala Met Gly
1               5                   10

<210> SEQ ID NO 21
<211> LENGTH: 10
<212> TYPE: PRT
<213> ORGANISM: Lama glama

<400> SEQUENCE: 21

Gly Phe Arg Phe Ala Glu Tyr Ala Ile Gly
1               5                   10

<210> SEQ ID NO 22
<211> LENGTH: 10
<212> TYPE: PRT
<213> ORGANISM: Lama glama

<400> SEQUENCE: 22

Gly Arg Thr Phe Ser Arg Phe Ala Met Gly
1               5                   10

<210> SEQ ID NO 23
<211> LENGTH: 10
<212> TYPE: PRT
<213> ORGANISM: Lama glama

<400> SEQUENCE: 23

Gly Phe Thr Phe Val Asp Tyr Ser Met Thr
1               5                   10

<210> SEQ ID NO 24
<211> LENGTH: 10
<212> TYPE: PRT
<213> ORGANISM: Lama glama
```

```
<400> SEQUENCE: 24

Gly Phe Thr Phe Ser Asn Tyr Tyr Met Tyr
 1               5                  10

<210> SEQ ID NO 25
<211> LENGTH: 10
<212> TYPE: PRT
<213> ORGANISM: Lama glama

<400> SEQUENCE: 25

Gly Gly Thr Phe Thr Asp Tyr Ala Met Gly
 1               5                  10

<210> SEQ ID NO 26
<211> LENGTH: 10
<212> TYPE: PRT
<213> ORGANISM: Lama glama

<400> SEQUENCE: 26

Gly Gly Thr Phe Thr Asp Tyr Ala Met Gly
 1               5                  10

<210> SEQ ID NO 27
<211> LENGTH: 10
<212> TYPE: PRT
<213> ORGANISM: Lama glama

<400> SEQUENCE: 27

Gly Phe Thr Phe Ser Asn Tyr Tyr Met Tyr
 1               5                  10

<210> SEQ ID NO 28
<211> LENGTH: 10
<212> TYPE: PRT
<213> ORGANISM: Lama glama

<400> SEQUENCE: 28

Gly Asn Thr Ile Ser Asp Tyr Ala Thr Gly
 1               5                  10

<210> SEQ ID NO 29
<211> LENGTH: 17
<212> TYPE: PRT
<213> ORGANISM: Lama glama

<400> SEQUENCE: 29

Gly Ile Tyr Ser Asp Ser Ser Ile Thr Ala Tyr Ala Asp Ser Val Lys
 1               5                  10                  15

Gly

<210> SEQ ID NO 30
<211> LENGTH: 17
<212> TYPE: PRT
<213> ORGANISM: Lama glama

<400> SEQUENCE: 30

Ser Ile Lys Trp Ser Gly Gly Asn Thr Tyr Tyr Ala Asp Ser Val Lys
 1               5                  10                  15

Gly

<210> SEQ ID NO 31
<211> LENGTH: 17
<212> TYPE: PRT
```

<213> ORGANISM: Lama glama

<400> SEQUENCE: 31

Ala Ile Arg Trp Ser Asp Gly Asn Thr Tyr Tyr Ala Asp Ser Val Lys
1               5                   10                  15

Gly

<210> SEQ ID NO 32
<211> LENGTH: 16
<212> TYPE: PRT
<213> ORGANISM: Lama glama

<400> SEQUENCE: 32

Trp Ile Thr Ser Gly Gly Ala Thr Tyr Tyr Ala Asp Ser Met Lys Gly
1               5                   10                  15

<210> SEQ ID NO 33
<211> LENGTH: 17
<212> TYPE: PRT
<213> ORGANISM: Lama glama

<400> SEQUENCE: 33

Gly Ile Asn Trp Asn Gly Val Lys Thr Arg Tyr Ser Asp Ser Met Asn
1               5                   10                  15

Asp

<210> SEQ ID NO 34
<211> LENGTH: 17
<212> TYPE: PRT
<213> ORGANISM: Lama glama

<400> SEQUENCE: 34

Ala Val Thr Trp Ser Gly Tyr Ser Val Tyr Tyr Ala Lys Ser Pro Lys
1               5                   10                  15

Gly

<210> SEQ ID NO 35
<211> LENGTH: 17
<212> TYPE: PRT
<213> ORGANISM: Lama glama

<400> SEQUENCE: 35

Gly Ile Gly Trp Ser Gly Gly Arg Ile Ile Val Ala Asp Ser Val Lys
1               5                   10                  15

Gly

<210> SEQ ID NO 36
<211> LENGTH: 17
<212> TYPE: PRT
<213> ORGANISM: Lama glama

<400> SEQUENCE: 36

Gly Ile Ser Trp Thr Ser Gly Thr Thr Tyr Phe Ala Asp Ser Val Lys
1               5                   10                  15

Gly

<210> SEQ ID NO 37
<211> LENGTH: 17
<212> TYPE: PRT
<213> ORGANISM: Lama glama

<400> SEQUENCE: 37

```
Ala Val Ser Arg Thr Gly Glu Thr Thr Asp Tyr Ala Asp Ala Val Lys
 1               5                  10                  15
Gly
```

<210> SEQ ID NO 38
<211> LENGTH: 17
<212> TYPE: PRT
<213> ORGANISM: Lama glama

<400> SEQUENCE: 38

```
Ala Ile Asn Trp Arg Gly Val Ser Thr Tyr Tyr Ala Asp Ser Val Lys
 1               5                  10                  15
Gly
```

<210> SEQ ID NO 39
<211> LENGTH: 17
<212> TYPE: PRT
<213> ORGANISM: Lama glama

<400> SEQUENCE: 39

```
Thr Ile Ser Arg Ile Gly Ser Thr Thr Tyr Tyr Ala Asp Ser Val Lys
 1               5                  10                  15
Gly
```

<210> SEQ ID NO 40
<211> LENGTH: 17
<212> TYPE: PRT
<213> ORGANISM: Lama glama

<400> SEQUENCE: 40

```
Ala Met Thr Arg Asn Ser Gly Ser Thr Tyr Tyr Ala Asp Ser Val Lys
 1               5                  10                  15
Gly
```

<210> SEQ ID NO 41
<211> LENGTH: 17
<212> TYPE: PRT
<213> ORGANISM: Lama glama

<400> SEQUENCE: 41

```
Ala Ile Ser Trp Ser Gly Gly Thr Thr Tyr Gly Ala Asp Ser Ala Lys
 1               5                  10                  15
Gly
```

<210> SEQ ID NO 42
<211> LENGTH: 16
<212> TYPE: PRT
<213> ORGANISM: Lama glama

<400> SEQUENCE: 42

```
Ala Ile Thr Leu Asp Gly Arg Thr Asn Tyr Ala Tyr Tyr Ala Glu Gly
 1               5                  10                  15
```

<210> SEQ ID NO 43
<211> LENGTH: 17
<212> TYPE: PRT
<213> ORGANISM: Lama glama

<400> SEQUENCE: 43

```
Ala Ile Ser Trp Ser Gly Gly Ser Thr Tyr Tyr Ala Asp Ser Val Lys
 1               5                  10                  15
Gly
```

<210> SEQ ID NO 44
<211> LENGTH: 17
<212> TYPE: PRT
<213> ORGANISM: Lama glama

<400> SEQUENCE: 44

Gln Ile Asn Thr Gly Gly Asp Ile Thr Thr Tyr Ser Asp Ser Val Lys
 1               5                  10                  15
Gly

<210> SEQ ID NO 45
<211> LENGTH: 17
<212> TYPE: PRT
<213> ORGANISM: Lama glama

<400> SEQUENCE: 45

Ser Ile Asp Trp Asn Ser Gly Arg Thr Asn Tyr Ala Asp Ser Val Lys
 1               5                  10                  15
Gly

<210> SEQ ID NO 46
<211> LENGTH: 17
<212> TYPE: PRT
<213> ORGANISM: Lama glama

<400> SEQUENCE: 46

Val Ile Gly Gly Gly Gly Asn Thr Tyr His Ala Ala Asp Ser Leu Lys
 1               5                  10                  15
Asp

<210> SEQ ID NO 47
<211> LENGTH: 17
<212> TYPE: PRT
<213> ORGANISM: Lama glama

<400> SEQUENCE: 47

Ala Ile Ser Arg Asn Ser Val Gly Thr Tyr Tyr Arg Asp Ser Val Lys
 1               5                  10                  15
Gly

<210> SEQ ID NO 48
<211> LENGTH: 17
<212> TYPE: PRT
<213> ORGANISM: Lama glama

<400> SEQUENCE: 48

Ala Ile Ser Ala Ser Gly Gly Asn Gln Tyr Tyr Lys Tyr Phe Ala Lys
 1               5                  10                  15
Gly

<210> SEQ ID NO 49
<211> LENGTH: 17
<212> TYPE: PRT
<213> ORGANISM: Lama glama

<400> SEQUENCE: 49

Tyr Ile Ser Thr Ser Asp Lys Thr Thr Tyr Tyr Ser Asp Phe Ala Glu
 1               5                  10                  15
Gly

```
<210> SEQ ID NO 50
<211> LENGTH: 17
<212> TYPE: PRT
<213> ORGANISM: Lama glama

<400> SEQUENCE: 50

Ala Ile Ser Trp Ser Gly Gly Thr Ala Tyr Gly Ala Asp Ser Ala Lys
 1               5                  10                  15
Gly

<210> SEQ ID NO 51
<211> LENGTH: 17
<212> TYPE: PRT
<213> ORGANISM: Lama glama

<400> SEQUENCE: 51

Ala Ile Asn Trp Asn Gly Arg Leu Thr Tyr Tyr Ala Glu Ser Met Lys
 1               5                  10                  15
Gly

<210> SEQ ID NO 52
<211> LENGTH: 17
<212> TYPE: PRT
<213> ORGANISM: Lama glama

<400> SEQUENCE: 52

Met Val Asn Thr Gly Gly Gly Thr Arg Tyr Ala Asp Ser Val Arg
 1               5                  10                  15
Gly

<210> SEQ ID NO 53
<211> LENGTH: 17
<212> TYPE: PRT
<213> ORGANISM: Lama glama

<400> SEQUENCE: 53

Ala Ile Ile Thr Ser Gly Arg Ser Thr Tyr Tyr Ala Asp Ser Val Lys
 1               5                  10                  15
Gly

<210> SEQ ID NO 54
<211> LENGTH: 17
<212> TYPE: PRT
<213> ORGANISM: Lama glama

<400> SEQUENCE: 54

Ala Ile Asn Trp Gly Gly Tyr Ser Thr Tyr Tyr Ser Asp Ala Val Lys
 1               5                  10                  15
Gly

<210> SEQ ID NO 55
<211> LENGTH: 17
<212> TYPE: PRT
<213> ORGANISM: Lama glama

<400> SEQUENCE: 55

Met Val Asn Thr Gly Gly Gly Gly Thr Arg Tyr Ala Asp Ser Val Arg
 1               5                  10                  15
Gly

<210> SEQ ID NO 56
<211> LENGTH: 17
```

```
<212> TYPE: PRT
<213> ORGANISM: Lama glama

<400> SEQUENCE: 56

Ser Ile Gly Arg Arg Thr Gly Trp Gln Val Tyr Ser Asp Ser Val Lys
 1               5                  10                  15

Gly

<210> SEQ ID NO 57
<211> LENGTH: 12
<212> TYPE: PRT
<213> ORGANISM: Lama glama

<400> SEQUENCE: 57

Met Val Met Gly Pro Ala Ala Thr Gly Tyr Glu Tyr
 1               5                  10

<210> SEQ ID NO 58
<211> LENGTH: 17
<212> TYPE: PRT
<213> ORGANISM: Lama glama

<400> SEQUENCE: 58

Gly Ser Lys Tyr Gly Gly Ser Trp Ser Arg Ser Gln Asp Ala Tyr Asn
 1               5                  10                  15

Tyr

<210> SEQ ID NO 59
<211> LENGTH: 17
<212> TYPE: PRT
<213> ORGANISM: Lama glama

<400> SEQUENCE: 59

Gly Ile Gly Thr Phe Gly Ser Ser Trp Thr Arg Ala Asp Arg Tyr Arg
 1               5                  10                  15

Tyr

<210> SEQ ID NO 60
<211> LENGTH: 6
<212> TYPE: PRT
<213> ORGANISM: Lama glama

<400> SEQUENCE: 60

Arg Val Pro Leu Asp Tyr
 1               5

<210> SEQ ID NO 61
<211> LENGTH: 16
<212> TYPE: PRT
<213> ORGANISM: Lama glama

<400> SEQUENCE: 61

Asp Gln Arg Phe Asp Gly Asp Asp Trp Ser Pro Ser Ala Phe Thr Arg
 1               5                  10                  15

<210> SEQ ID NO 62
<211> LENGTH: 16
<212> TYPE: PRT
<213> ORGANISM: Lama glama

<400> SEQUENCE: 62

Val Phe Val Arg Thr Ala Gly Val Pro Thr Leu Gly Glu Tyr Asp Tyr
 1               5                  10                  15
```

```
<210> SEQ ID NO 63
<211> LENGTH: 15
<212> TYPE: PRT
<213> ORGANISM: Lama glama

<400> SEQUENCE: 63

Thr Lys Gln Phe Phe Pro Leu Ser Asn Ser Val Trp Tyr Asp Tyr
1               5                   10                  15

<210> SEQ ID NO 64
<211> LENGTH: 20
<212> TYPE: PRT
<213> ORGANISM: Lama glama

<400> SEQUENCE: 64

Ser Glu Arg Asp Phe Tyr Thr Arg Asn Tyr Tyr Phe Thr Phe Glu Ser
1               5                   10                  15

Leu Tyr Asp Tyr
            20

<210> SEQ ID NO 65
<211> LENGTH: 17
<212> TYPE: PRT
<213> ORGANISM: Lama glama

<400> SEQUENCE: 65

Asp Tyr Asn Leu Gly Thr Phe Val Thr Arg Lys Asp Ser Met Tyr Asp
1               5                   10                  15

Phe

<210> SEQ ID NO 66
<211> LENGTH: 15
<212> TYPE: PRT
<213> ORGANISM: Lama glama

<400> SEQUENCE: 66

Arg Arg Asn Phe Phe Gly Asn Asn Ser Ala Gly Gln Tyr Ala Tyr
1               5                   10                  15

<210> SEQ ID NO 67
<211> LENGTH: 12
<212> TYPE: PRT
<213> ORGANISM: Lama glama

<400> SEQUENCE: 67

Ser Arg Tyr Val Leu Lys Tyr Asp Lys Asp Ala Tyr
1               5                   10

<210> SEQ ID NO 68
<211> LENGTH: 17
<212> TYPE: PRT
<213> ORGANISM: Lama glama

<400> SEQUENCE: 68

Lys Ala Ser Met Tyr Gly Ser Thr Leu Tyr Pro Pro Thr Gly Tyr Asn
1               5                   10                  15

Tyr

<210> SEQ ID NO 69
<211> LENGTH: 9
<212> TYPE: PRT
<213> ORGANISM: Lama glama

<400> SEQUENCE: 69
```

Gly Arg Ala Val Ser Asp Tyr Asp Tyr
1               5

<210> SEQ ID NO 70
<211> LENGTH: 13
<212> TYPE: PRT
<213> ORGANISM: Lama glama

<400> SEQUENCE: 70

Leu Arg Ser Arg Ala Val Met Asp Thr Ile Pro Asn Tyr
1               5                   10

<210> SEQ ID NO 71
<211> LENGTH: 17
<212> TYPE: PRT
<213> ORGANISM: Lama glama

<400> SEQUENCE: 71

Asp Arg Arg Arg Tyr Tyr Ser Gly Ser Tyr Pro Pro Ser Glu Tyr Asp
1               5                   10                  15

Tyr

<210> SEQ ID NO 72
<211> LENGTH: 14
<212> TYPE: PRT
<213> ORGANISM: Lama glama

<400> SEQUENCE: 72

Ala Arg Ser Val Pro Leu Ser Asp Pro Arg Thr Tyr Ser Ser
1               5                   10

<210> SEQ ID NO 73
<211> LENGTH: 14
<212> TYPE: PRT
<213> ORGANISM: Lama glama

<400> SEQUENCE: 73

Ala Ala Ala Ala Ser Thr Leu Val Gly Gly Ser Tyr Asp Tyr
1               5                   10

<210> SEQ ID NO 74
<211> LENGTH: 22
<212> TYPE: PRT
<213> ORGANISM: Lama glama

<400> SEQUENCE: 74

Asp Arg Asp Phe Thr Ile Val Ala Gly Phe Ile Arg Ser Gln Tyr Ser
1               5                   10                  15

Pro Arg Ala Val Glu Tyr
            20

<210> SEQ ID NO 75
<211> LENGTH: 15
<212> TYPE: PRT
<213> ORGANISM: Lama glama

<400> SEQUENCE: 75

Asp Pro Met Tyr Gly Arg Ser Val Met Ser Thr Arg Tyr Asn Tyr
1               5                   10                  15

<210> SEQ ID NO 76
<211> LENGTH: 18
<212> TYPE: PRT
<213> ORGANISM: Lama glama

```
<400> SEQUENCE: 76

Ala Thr Lys Gln Phe Ser Asn Ala Tyr Ser Asp Tyr Val His Asp Tyr
 1               5                  10                  15

Asp Tyr

<210> SEQ ID NO 77
<211> LENGTH: 17
<212> TYPE: PRT
<213> ORGANISM: Lama glama

<400> SEQUENCE: 77

Gly Leu Tyr Tyr Ser Asp Tyr Arg Thr Pro Glu Tyr Thr Glu Tyr Val
 1               5                  10                  15

His

<210> SEQ ID NO 78
<211> LENGTH: 9
<212> TYPE: PRT
<213> ORGANISM: Lama glama

<400> SEQUENCE: 78

Gly Arg Ala Val Ser Asp Tyr Asp Tyr
 1               5

<210> SEQ ID NO 79
<211> LENGTH: 12
<212> TYPE: PRT
<213> ORGANISM: Lama glama

<400> SEQUENCE: 79

Gly Glu Leu Tyr Gly Met Gly Ser Lys His Asp Tyr
 1               5                  10

<210> SEQ ID NO 80
<211> LENGTH: 11
<212> TYPE: PRT
<213> ORGANISM: Lama glama

<400> SEQUENCE: 80

Asp Arg Pro Gln Ser Gly Trp Ser Met Asp Tyr
 1               5                  10

<210> SEQ ID NO 81
<211> LENGTH: 13
<212> TYPE: PRT
<213> ORGANISM: Lama glama

<400> SEQUENCE: 81

Thr Lys Trp Val Val Arg Arg Pro Ala Asp Tyr Asn Tyr
 1               5                  10

<210> SEQ ID NO 82
<211> LENGTH: 12
<212> TYPE: PRT
<213> ORGANISM: Lama glama

<400> SEQUENCE: 82

Asp Pro Gln Leu Ile Thr Thr Pro Glu Tyr Asn Tyr
 1               5                  10

<210> SEQ ID NO 83
<211> LENGTH: 11
<212> TYPE: PRT
```

<213> ORGANISM: Lama glama

<400> SEQUENCE: 83

Asp Arg Pro Gln Ser Gly Trp Ser Met Asp Tyr
1               5                   10

<210> SEQ ID NO 84
<211> LENGTH: 18
<212> TYPE: PRT
<213> ORGANISM: Lama glama

<400> SEQUENCE: 84

Ser Gln Asp Ser Gly Phe Asp Thr Pro Val Thr Glu Ser His Leu Tyr
1               5                   10                  15

Gly Tyr

<210> SEQ ID NO 85
<211> LENGTH: 10
<212> TYPE: PRT
<213> ORGANISM: Lama glama

<400> SEQUENCE: 85

Gly Phe Thr Phe Ser Ser Tyr Ala Met Ser
1               5                   10

<210> SEQ ID NO 86
<211> LENGTH: 10
<212> TYPE: PRT
<213> ORGANISM: Lama glama

<400> SEQUENCE: 86

Gly Phe Thr Phe Ser Ser Tyr Tyr Met Ser
1               5                   10

<210> SEQ ID NO 87
<211> LENGTH: 10
<212> TYPE: PRT
<213> ORGANISM: Lama glama

<400> SEQUENCE: 87

Gly Phe Thr Phe Asp Glu His Ala Ile Gly
1               5                   10

<210> SEQ ID NO 88
<211> LENGTH: 10
<212> TYPE: PRT
<213> ORGANISM: Lama glama

<400> SEQUENCE: 88

Gly Phe Thr Val Ser Ser Asn His Met Thr
1               5                   10

<210> SEQ ID NO 89
<211> LENGTH: 10
<212> TYPE: PRT
<213> ORGANISM: Lama glama

<400> SEQUENCE: 89

Gly Phe Thr Phe Ser Ser Tyr His Met Ala
1               5                   10

<210> SEQ ID NO 90
<211> LENGTH: 10
<212> TYPE: PRT
<213> ORGANISM: Lama glama

```
<400> SEQUENCE: 90

Gly Phe Thr Phe Asp Glu His Ala Ile Gly
 1               5                  10

<210> SEQ ID NO 91
<211> LENGTH: 10
<212> TYPE: PRT
<213> ORGANISM: Lama glama

<400> SEQUENCE: 91

Gly Phe Thr Phe Ser Arg His Gln Met Ser
 1               5                  10

<210> SEQ ID NO 92
<211> LENGTH: 10
<212> TYPE: PRT
<213> ORGANISM: Lama glama

<400> SEQUENCE: 92

Gly Phe Thr Phe Arg Thr Tyr Tyr Met Asn
 1               5                  10

<210> SEQ ID NO 93
<211> LENGTH: 10
<212> TYPE: PRT
<213> ORGANISM: Lama glama

<400> SEQUENCE: 93

Gly Phe Ile Phe Ser Ser Tyr Ala Met Ser
 1               5                  10

<210> SEQ ID NO 94
<211> LENGTH: 10
<212> TYPE: PRT
<213> ORGANISM: Lama glama

<400> SEQUENCE: 94

Gly Phe Ile Phe Ser Ser Tyr Ala Met Ser
 1               5                  10

<210> SEQ ID NO 95
<211> LENGTH: 10
<212> TYPE: PRT
<213> ORGANISM: Lama glama

<400> SEQUENCE: 95

Gly Phe Thr Phe Ser Thr Tyr Ala Met Thr
 1               5                  10

<210> SEQ ID NO 96
<211> LENGTH: 10
<212> TYPE: PRT
<213> ORGANISM: Lama glama

<400> SEQUENCE: 96

Gly Phe Thr Phe Ser Ser Tyr Ala Met Ser
 1               5                  10

<210> SEQ ID NO 97
<211> LENGTH: 10
<212> TYPE: PRT
<213> ORGANISM: Lama glama

<400> SEQUENCE: 97
```

```
Gly Phe Thr Phe Ser Arg His Gln Met Ser
1               5                   10

<210> SEQ ID NO 98
<211> LENGTH: 10
<212> TYPE: PRT
<213> ORGANISM: Lama glama

<400> SEQUENCE: 98

Gly Phe Thr Phe Ser Arg Tyr Ala Met Ser
1               5                   10

<210> SEQ ID NO 99
<211> LENGTH: 10
<212> TYPE: PRT
<213> ORGANISM: Lama glama

<400> SEQUENCE: 99

Gly Phe Thr Phe Ser Gly Tyr Ala Met Ser
1               5                   10

<210> SEQ ID NO 100
<211> LENGTH: 10
<212> TYPE: PRT
<213> ORGANISM: Lama glama

<400> SEQUENCE: 100

Gly Phe Ala Phe Ser Asn Tyr Arg Met Thr
1               5                   10

<210> SEQ ID NO 101
<211> LENGTH: 10
<212> TYPE: PRT
<213> ORGANISM: Lama glama

<400> SEQUENCE: 101

Gly Phe Thr Phe Ser Arg Tyr Ala Met Ser
1               5                   10

<210> SEQ ID NO 102
<211> LENGTH: 17
<212> TYPE: PRT
<213> ORGANISM: Lama glama

<400> SEQUENCE: 102

Gly Ile Glu Gly Gly Gly Gly Ile Thr Arg Tyr Ala Asp Ser Val Lys
1               5                   10                  15

Gly

<210> SEQ ID NO 103
<211> LENGTH: 17
<212> TYPE: PRT
<213> ORGANISM: Lama glama

<400> SEQUENCE: 103

Thr Ile Lys Pro Gly Gly Gly Ser Thr Tyr Tyr Ala Asp Ser Val Lys
1               5                   10                  15

Gly

<210> SEQ ID NO 104
<211> LENGTH: 16
<212> TYPE: PRT
<213> ORGANISM: Lama glama

<400> SEQUENCE: 104
```

```
Thr Ile Asp Ile Gly Gly Gly Arg Thr Tyr Ala Asp Ser Val Lys Gly
1               5                   10                  15

<210> SEQ ID NO 105
<211> LENGTH: 17
<212> TYPE: PRT
<213> ORGANISM: Lama glama

<400> SEQUENCE: 105

Arg Ile Ser Ser Asp Gly Arg Asn Thr Tyr Tyr Ala Asp Ser Val Lys
1               5                   10                  15

Gly

<210> SEQ ID NO 106
<211> LENGTH: 17
<212> TYPE: PRT
<213> ORGANISM: Lama glama

<400> SEQUENCE: 106

Thr Ile Asn Pro Gly Asp Gly Ser Thr Tyr Tyr Ala Asp Ser Val Lys
1               5                   10                  15

Gly

<210> SEQ ID NO 107
<211> LENGTH: 16
<212> TYPE: PRT
<213> ORGANISM: Lama glama

<400> SEQUENCE: 107

His Ile Asp Thr Gly Gly Ser Thr Trp Tyr Ala Ala Ser Val Lys Gly
1               5                   10                  15

<210> SEQ ID NO 108
<211> LENGTH: 16
<212> TYPE: PRT
<213> ORGANISM: Lama glama

<400> SEQUENCE: 108

His Ile Asp Thr Gly Gly Ser Thr Trp Tyr Ala Ala Ser Val Lys Gly
1               5                   10                  15

<210> SEQ ID NO 109
<211> LENGTH: 17
<212> TYPE: PRT
<213> ORGANISM: Lama glama

<400> SEQUENCE: 109

Thr Ile Asn Ile Asp Gly Ser Ser Thr Tyr Tyr Ala Asp Ser Val Arg
1               5                   10                  15

Gly

<210> SEQ ID NO 110
<211> LENGTH: 17
<212> TYPE: PRT
<213> ORGANISM: Lama glama

<400> SEQUENCE: 110

Gly Ile Asn Ser Phe Gly Gly Ser Lys Tyr Tyr Ala Asp Ser Val Lys
1               5                   10                  15

Gly

<210> SEQ ID NO 111
```

-continued

```
<211> LENGTH: 17
<212> TYPE: PRT
<213> ORGANISM: Lama glama

<400> SEQUENCE: 111

Gly Ile Asn Ser Phe Gly Gly Ser Lys Tyr Tyr Ala Asp Ser Val Lys
1               5                   10                  15

Gly

<210> SEQ ID NO 112
<211> LENGTH: 17
<212> TYPE: PRT
<213> ORGANISM: Lama glama

<400> SEQUENCE: 112

Thr Ile Asn Thr Ser Gly Arg Gly Thr Tyr Tyr Ala Asp Ser Val Lys
1               5                   10                  15

Gly

<210> SEQ ID NO 113
<211> LENGTH: 17
<212> TYPE: PRT
<213> ORGANISM: Lama glama

<400> SEQUENCE: 113

Ala Ile Asn Ser Gly Gly Gly Ser Thr Ser Tyr Ala Asp Ser Val Lys
1               5                   10                  15

Gly

<210> SEQ ID NO 114
<211> LENGTH: 17
<212> TYPE: PRT
<213> ORGANISM: Lama glama

<400> SEQUENCE: 114

His Ile Asp Thr Gly Gly Gly Ser Thr Trp Tyr Ala Ala Ser Val Lys
1               5                   10                  15

Gly

<210> SEQ ID NO 115
<211> LENGTH: 17
<212> TYPE: PRT
<213> ORGANISM: Lama glama

<400> SEQUENCE: 115

Asp Ile Asn Ser Gly Gly Asp Ser Thr Arg Asn Ala Asp Ser Val Lys
1               5                   10                  15

Gly

<210> SEQ ID NO 116
<211> LENGTH: 17
<212> TYPE: PRT
<213> ORGANISM: Lama glama

<400> SEQUENCE: 116

Ser Ile Asn Ser Gly Gly Gly Ser Thr Tyr Tyr Ala Asp Ser Val Lys
1               5                   10                  15

Gly

<210> SEQ ID NO 117
<211> LENGTH: 17
<212> TYPE: PRT
```

<213> ORGANISM: Lama glama

<400> SEQUENCE: 117

Arg Ile Asn Ser Ile Gly Asp Arg Ile Ser Tyr Ala Asp Ser Val Lys
1               5                   10                  15

Gly

<210> SEQ ID NO 118
<211> LENGTH: 17
<212> TYPE: PRT
<213> ORGANISM: Lama glama

<400> SEQUENCE: 118

Asp Ile Asn Ser Gly Gly Asp Ser Thr Arg Asn Ala Asp Ser Val Lys
1               5                   10                  15

Gly

<210> SEQ ID NO 119
<211> LENGTH: 10
<212> TYPE: PRT
<213> ORGANISM: Lama glama

<400> SEQUENCE: 119

Ala His Gly Gly Tyr Gly Ala Phe Gly Ser
1               5                   10

<210> SEQ ID NO 120
<211> LENGTH: 10
<212> TYPE: PRT
<213> ORGANISM: Lama glama

<400> SEQUENCE: 120

Ala His Gly Gly Tyr Gly Ala Phe Gly Ser
1               5                   10

<210> SEQ ID NO 121
<211> LENGTH: 10
<212> TYPE: PRT
<213> ORGANISM: Lama glama

<400> SEQUENCE: 121

Ala His Gly Gly Tyr Gly Ala Phe Gly Ser
1               5                   10

<210> SEQ ID NO 122
<211> LENGTH: 8
<212> TYPE: PRT
<213> ORGANISM: Lama glama

<400> SEQUENCE: 122

Tyr Ser Gly Gly Ala Leu Asp Ala
1               5

<210> SEQ ID NO 123
<211> LENGTH: 8
<212> TYPE: PRT
<213> ORGANISM: Lama glama

<400> SEQUENCE: 123

Tyr Ser Gly Gly Ala Leu Asp Ala
1               5

<210> SEQ ID NO 124
<211> LENGTH: 8

```
<212> TYPE: PRT
<213> ORGANISM: Lama glama

<400> SEQUENCE: 124

Leu Ser Gln Gly Ala Met Asp Tyr
 1               5

<210> SEQ ID NO 125
<211> LENGTH: 8
<212> TYPE: PRT
<213> ORGANISM: Lama glama

<400> SEQUENCE: 125

Leu Ser Gln Gly Ala Met Asp Tyr
 1               5

<210> SEQ ID NO 126
<211> LENGTH: 8
<212> TYPE: PRT
<213> ORGANISM: Lama glama

<400> SEQUENCE: 126

Leu Ser Gln Gly Ala Met Asp Tyr
 1               5

<210> SEQ ID NO 127
<211> LENGTH: 9
<212> TYPE: PRT
<213> ORGANISM: Lama glama

<400> SEQUENCE: 127

Ile Asp Arg Glu Arg Ala Phe Thr Ser
 1               5

<210> SEQ ID NO 128
<211> LENGTH: 9
<212> TYPE: PRT
<213> ORGANISM: Lama glama

<400> SEQUENCE: 128

Ile Asp Trp Glu Arg Ala Phe Thr Ser
 1               5

<210> SEQ ID NO 129
<211> LENGTH: 9
<212> TYPE: PRT
<213> ORGANISM: Lama glama

<400> SEQUENCE: 129

Gln Gly Tyr Ala Gly Ser Tyr Asp Tyr
 1               5

<210> SEQ ID NO 130
<211> LENGTH: 9
<212> TYPE: PRT
<213> ORGANISM: Lama glama

<400> SEQUENCE: 130

Leu Gly Val Pro Gly Thr Phe Asp Tyr
 1               5

<210> SEQ ID NO 131
<211> LENGTH: 8
<212> TYPE: PRT
<213> ORGANISM: Lama glama
```

```
<400> SEQUENCE: 131

Thr Asn Arg Gly Ile Phe Asp Tyr
1               5

<210> SEQ ID NO 132
<211> LENGTH: 10
<212> TYPE: PRT
<213> ORGANISM: Lama glama

<400> SEQUENCE: 132

Thr Pro Gly Ser Ser Gly Val Tyr Glu Tyr
1               5                   10

<210> SEQ ID NO 133
<211> LENGTH: 8
<212> TYPE: PRT
<213> ORGANISM: Lama glama

<400> SEQUENCE: 133

Thr Gln Thr Gly Ser His Asp Tyr
1               5

<210> SEQ ID NO 134
<211> LENGTH: 8
<212> TYPE: PRT
<213> ORGANISM: Lama glama

<400> SEQUENCE: 134

Gln Val Gly Thr Ala Tyr Asp Tyr
1               5

<210> SEQ ID NO 135
<211> LENGTH: 10
<212> TYPE: PRT
<213> ORGANISM: Lama glama

<400> SEQUENCE: 135

Arg Arg Gly Ser Ser Gly Val Tyr Glu Tyr
1               5                   10

<210> SEQ ID NO 136
<211> LENGTH: 10
<212> TYPE: PRT
<213> ORGANISM: Lama glama

<400> SEQUENCE: 136

Gly Ser Arg Arg Ser Phe Asn Val Met Gly
1               5                   10

<210> SEQ ID NO 137
<211> LENGTH: 10
<212> TYPE: PRT
<213> ORGANISM: Lama glama

<400> SEQUENCE: 137

Gly Asp Thr Phe Ser Ile Asn Ala Tyr Gly
1               5                   10

<210> SEQ ID NO 138
<211> LENGTH: 10
<212> TYPE: PRT
<213> ORGANISM: Lama glama

<400> SEQUENCE: 138

Gly Phe Thr Phe Arg Asp Tyr Trp Met Tyr
```

<210> SEQ ID NO 139
<211> LENGTH: 10
<212> TYPE: PRT
<213> ORGANISM: Lama glama

<400> SEQUENCE: 139

Gly Ile Thr Phe Ser Glu Lys His Met Ala
1               5                   10

<210> SEQ ID NO 140
<211> LENGTH: 10
<212> TYPE: PRT
<213> ORGANISM: Lama glama

<400> SEQUENCE: 140

Gly Arg Thr Phe Ser Ser Tyr Gly Met Gly
1               5                   10

<210> SEQ ID NO 141
<211> LENGTH: 10
<212> TYPE: PRT
<213> ORGANISM: Lama glama

<400> SEQUENCE: 141

Gly Arg Thr Phe Ser Ser Tyr Gly Met Gly
1               5                   10

<210> SEQ ID NO 142
<211> LENGTH: 10
<212> TYPE: PRT
<213> ORGANISM: Lama glama

<400> SEQUENCE: 142

Gly Thr Ser Ser Gly Ile Asn Ala Met Val
1               5                   10

<210> SEQ ID NO 143
<211> LENGTH: 10
<212> TYPE: PRT
<213> ORGANISM: Lama glama

<400> SEQUENCE: 143

Gly Arg Thr Phe Ser Ser Tyr Ser Met Ala
1               5                   10

<210> SEQ ID NO 144
<211> LENGTH: 10
<212> TYPE: PRT
<213> ORGANISM: Lama glama

<400> SEQUENCE: 144

Val Ser Thr Phe Ser Ile Gly Ala Ile Gly
1               5                   10

<210> SEQ ID NO 145
<211> LENGTH: 10
<212> TYPE: PRT
<213> ORGANISM: Lama glama

<400> SEQUENCE: 145

Gly Ser Thr Phe Ser Gly Asn Asp Ile Gly
1               5                   10

```
<210> SEQ ID NO 146
<211> LENGTH: 10
<212> TYPE: PRT
<213> ORGANISM: Lama glama

<400> SEQUENCE: 146

Gly Arg Thr Phe Ser Ser Tyr Gly Met Gly
 1               5                  10

<210> SEQ ID NO 147
<211> LENGTH: 10
<212> TYPE: PRT
<213> ORGANISM: Lama glama

<400> SEQUENCE: 147

Gly Arg Thr Phe Ser Asp Ile Ala Met Ala
 1               5                  10

<210> SEQ ID NO 148
<211> LENGTH: 10
<212> TYPE: PRT
<213> ORGANISM: Lama glama

<400> SEQUENCE: 148

Gly Gln Thr Leu Asn Thr Tyr Val Met Gly
 1               5                  10

<210> SEQ ID NO 149
<211> LENGTH: 10
<212> TYPE: PRT
<213> ORGANISM: Lama glama

<400> SEQUENCE: 149

Gly Pro Thr Ser Ile Thr Tyr Gly Met Ala
 1               5                  10

<210> SEQ ID NO 150
<211> LENGTH: 10
<212> TYPE: PRT
<213> ORGANISM: Lama glama

<400> SEQUENCE: 150

Gly Gly Asp Val Ser Thr Tyr Ala Met Val
 1               5                  10

<210> SEQ ID NO 151
<211> LENGTH: 10
<212> TYPE: PRT
<213> ORGANISM: Lama glama

<400> SEQUENCE: 151

Gly Arg Thr Phe Gly Ser Tyr Thr Met Gly
 1               5                  10

<210> SEQ ID NO 152
<211> LENGTH: 10
<212> TYPE: PRT
<213> ORGANISM: Lama glama

<400> SEQUENCE: 152

Gly Arg Thr Phe Ser Ser Tyr Gly Met Gly
 1               5                  10

<210> SEQ ID NO 153
<211> LENGTH: 10
<212> TYPE: PRT
```

-continued

<213> ORGANISM: Lama glama

<400> SEQUENCE: 153

Gly Ser Leu Ser Arg Ile Thr Val Met Gly
1               5                   10

<210> SEQ ID NO 154
<211> LENGTH: 10
<212> TYPE: PRT
<213> ORGANISM: Lama glama

<400> SEQUENCE: 154

Gly Ser Ile Ser Ser Phe Asp Ala Met Ala
1               5                   10

<210> SEQ ID NO 155
<211> LENGTH: 10
<212> TYPE: PRT
<213> ORGANISM: Lama glama

<400> SEQUENCE: 155

Gly Arg Pro Phe Ser Ser Phe Ala Met Gly
1               5                   10

<210> SEQ ID NO 156
<211> LENGTH: 10
<212> TYPE: PRT
<213> ORGANISM: Lama glama

<400> SEQUENCE: 156

Gly Arg Thr Phe Ser Ser Tyr His Met Gly
1               5                   10

<210> SEQ ID NO 157
<211> LENGTH: 16
<212> TYPE: PRT
<213> ORGANISM: Lama glama

<400> SEQUENCE: 157

Thr Ile Thr Val Gly Asp Thr Thr Ser Tyr Ala Glu Ala Val Lys Gly
1               5                   10                  15

<210> SEQ ID NO 158
<211> LENGTH: 17
<212> TYPE: PRT
<213> ORGANISM: Lama glama

<400> SEQUENCE: 158

Ala Ile Ser Gly Arg Gly Thr Asn Thr Phe Val Ala Asp Ser Val Lys
1               5                   10                  15

Gly

<210> SEQ ID NO 159
<211> LENGTH: 17
<212> TYPE: PRT
<213> ORGANISM: Lama glama

<400> SEQUENCE: 159

Ser Ile Tyr Ser Asp Gly Ser Arg Thr Ala Tyr Ala Ala Ser Val Lys
1               5                   10                  15

Gly

<210> SEQ ID NO 160
<211> LENGTH: 16

```
<212> TYPE: PRT
<213> ORGANISM: Lama glama

<400> SEQUENCE: 160

Val Ile Thr Arg Gly Gly Thr Thr Asn Tyr Gly Asp Ser Val Lys Gly
 1               5                  10                  15

<210> SEQ ID NO 161
<211> LENGTH: 16
<212> TYPE: PRT
<213> ORGANISM: Lama glama

<400> SEQUENCE: 161

Gly Ile Thr Lys Asn Gly Val Thr Tyr Tyr Ala Pro Ser Val Thr Gly
 1               5                  10                  15

<210> SEQ ID NO 162
<211> LENGTH: 17
<212> TYPE: PRT
<213> ORGANISM: Lama glama

<400> SEQUENCE: 162

Ala Met Arg Glu Ser Gly Ala Asp Thr His Tyr Ala Asp Phe Val Arg
 1               5                  10                  15
Gly

<210> SEQ ID NO 163
<211> LENGTH: 17
<212> TYPE: PRT
<213> ORGANISM: Lama glama

<400> SEQUENCE: 163

Ala Met Arg Glu Ser Gly Ala Asp Thr His Tyr Ala Asp Phe Val Arg
 1               5                  10                  15
Gly

<210> SEQ ID NO 164
<211> LENGTH: 16
<212> TYPE: PRT
<213> ORGANISM: Lama glama

<400> SEQUENCE: 164

Thr Ile Thr Asn Ser Gly Lys Thr Asp Tyr Ala Ala Ser Ala Lys Gly
 1               5                  10                  15

<210> SEQ ID NO 165
<211> LENGTH: 17
<212> TYPE: PRT
<213> ORGANISM: Lama glama

<400> SEQUENCE: 165

Ala Ile Asn Trp Arg Ser Ser Val Thr Ala Tyr Ala Asp Ser Val Lys
 1               5                  10                  15
Gly

<210> SEQ ID NO 166
<211> LENGTH: 16
<212> TYPE: PRT
<213> ORGANISM: Lama glama

<400> SEQUENCE: 166

Gly Ile Ser Gly Gly Gly Ser Thr Tyr Tyr Thr Asp Ser Val Lys Gly
 1               5                  10                  15
```

```
<210> SEQ ID NO 167
<211> LENGTH: 16
<212> TYPE: PRT
<213> ORGANISM: Lama glama

<400> SEQUENCE: 167

Val Ile Ser Asp Gly Gly Tyr Thr Ser Tyr Ala Thr Ser Val Lys Gly
 1               5                  10                  15

<210> SEQ ID NO 168
<211> LENGTH: 17
<212> TYPE: PRT
<213> ORGANISM: Lama glama

<400> SEQUENCE: 168

Ala Ile Ser Trp Gly Ala Gly Thr Pro Tyr Tyr Ala Asp Ser Val Lys
 1               5                  10                  15

Gly

<210> SEQ ID NO 169
<211> LENGTH: 17
<212> TYPE: PRT
<213> ORGANISM: Lama glama

<400> SEQUENCE: 169

Ala Ile Asp Trp Asn Gly Gly Thr Thr Tyr Tyr Thr Thr Phe Val Lys
 1               5                  10                  15

Gly

<210> SEQ ID NO 170
<211> LENGTH: 17
<212> TYPE: PRT
<213> ORGANISM: Lama glama

<400> SEQUENCE: 170

Ala Ile Asn Trp Arg Asp Thr Ser Thr Tyr Tyr Gln Asp Ser Val Lys
 1               5                  10                  15

Gly

<210> SEQ ID NO 171
<211> LENGTH: 17
<212> TYPE: PRT
<213> ORGANISM: Lama glama

<400> SEQUENCE: 171

Ala Val Thr Pro Ser Gly Gly Ala Ala Tyr Ala Asp Ser Val Lys
 1               5                  10                  15

Gly

<210> SEQ ID NO 172
<211> LENGTH: 17
<212> TYPE: PRT
<213> ORGANISM: Lama glama

<400> SEQUENCE: 172

Leu Leu Ser Arg Ser Gly Arg Thr Thr Asn Tyr Ala Asp Ser Val Lys
 1               5                  10                  15

Gly

<210> SEQ ID NO 173
<211> LENGTH: 16
<212> TYPE: PRT
```

<213> ORGANISM: Lama glama

<400> SEQUENCE: 173

Arg Ile Asn Ser Ala Gly Arg Thr Met Tyr Ala Asp Ser Val Lys Gly
1               5                   10                  15

<210> SEQ ID NO 174
<211> LENGTH: 17
<212> TYPE: PRT
<213> ORGANISM: Lama glama

<400> SEQUENCE: 174

Ser Ile Asn Trp Arg Gly Ser Ser Thr Tyr Tyr Ala Asp Ser Val Lys
1               5                   10                  15

Gly

<210> SEQ ID NO 175
<211> LENGTH: 16
<212> TYPE: PRT
<213> ORGANISM: Lama glama

<400> SEQUENCE: 175

Ile Ile Thr Ser Ser Gly Gly Thr Asp Tyr Ala Asp Ser Val Lys Gly
1               5                   10                  15

<210> SEQ ID NO 176
<211> LENGTH: 16
<212> TYPE: PRT
<213> ORGANISM: Lama glama

<400> SEQUENCE: 176

Ile Ile Thr Ser Gly Gly Ala Thr Asn Tyr Ala Asp Ser Val Lys Gly
1               5                   10                  15

<210> SEQ ID NO 177
<211> LENGTH: 17
<212> TYPE: PRT
<213> ORGANISM: Lama glama

<400> SEQUENCE: 177

Ala Ile Ser Ala Ser Gly Gly Glu Thr Tyr Tyr Thr Gly Ser Leu Lys
1               5                   10                  15

Gly

<210> SEQ ID NO 178
<211> LENGTH: 15
<212> TYPE: DNA
<213> ORGANISM: Lama glama
<220> FEATURE:
<221> NAME/KEY: modified_base
<222> LOCATION: (2)
<223> OTHER INFORMATION: a, t, c, g, other or unknown

<400> SEQUENCE: 178
anwsgdttyy asvkg                                                15

<210> SEQ ID NO 179
<211> LENGTH: 17
<212> TYPE: PRT
<213> ORGANISM: Lama glama

<400> SEQUENCE: 179

Ala Ile Asn Trp Ser Gly Asp Thr Thr Tyr Tyr Glu Ala Ser Val Lys
1               5                   10                  15

Gly

<210> SEQ ID NO 180
<211> LENGTH: 11
<212> TYPE: PRT
<213> ORGANISM: Lama glama

<400> SEQUENCE: 180

Glu Glu Trp Leu Gly Val Arg Gln Asn Asn Tyr
 1               5                  10

<210> SEQ ID NO 181
<211> LENGTH: 3
<212> TYPE: PRT
<213> ORGANISM: Lama glama

<400> SEQUENCE: 181

Gly Glu Tyr
 1

<210> SEQ ID NO 182
<211> LENGTH: 12
<212> TYPE: PRT
<213> ORGANISM: Lama glama

<400> SEQUENCE: 182

Met Leu Leu Gly Pro Gly Ala Pro Gly Tyr Asp Tyr
 1               5                  10

<210> SEQ ID NO 183
<211> LENGTH: 9
<212> TYPE: PRT
<213> ORGANISM: Lama glama

<400> SEQUENCE: 183

Asp Phe Tyr Gly Leu Gly Phe Asp Tyr
 1               5

<210> SEQ ID NO 184
<211> LENGTH: 16
<212> TYPE: PRT
<213> ORGANISM: Lama glama

<400> SEQUENCE: 184

Ala Pro Lys Tyr Glu Gly Val Ser Asp Thr Ser Ser Asp Tyr Asn Tyr
 1               5                  10                  15

<210> SEQ ID NO 185
<211> LENGTH: 9
<212> TYPE: PRT
<213> ORGANISM: Lama glama

<400> SEQUENCE: 185

Leu Asp Ile Thr Thr Ala Ala Ser Tyr
 1               5

<210> SEQ ID NO 186
<211> LENGTH: 7
<212> TYPE: PRT
<213> ORGANISM: Lama glama

<400> SEQUENCE: 186

Thr Ile Asn Gly Ala Ala Arg
 1               5

```
<210> SEQ ID NO 187
<211> LENGTH: 7
<212> TYPE: PRT
<213> ORGANISM: Lama glama

<400> SEQUENCE: 187

Thr Ile Asn Gly Ala Ala Arg
 1               5

<210> SEQ ID NO 188
<211> LENGTH: 11
<212> TYPE: PRT
<213> ORGANISM: Lama glama

<400> SEQUENCE: 188

Glu Ala Leu Pro Gly Thr Tyr Gly Leu Asp Tyr
 1               5                  10

<210> SEQ ID NO 189
<211> LENGTH: 9
<212> TYPE: PRT
<213> ORGANISM: Lama glama

<400> SEQUENCE: 189

Ile Leu Ala Gly Gly Leu Leu Ala Phe
 1               5

<210> SEQ ID NO 190
<211> LENGTH: 7
<212> TYPE: PRT
<213> ORGANISM: Lama glama

<400> SEQUENCE: 190

Gly Gly Ser Ser Gly Thr Phe
 1               5

<210> SEQ ID NO 191
<211> LENGTH: 7
<212> TYPE: PRT
<213> ORGANISM: Lama glama

<400> SEQUENCE: 191

Thr Ile Asn Gly Ala Ala Arg
 1               5

<210> SEQ ID NO 192
<211> LENGTH: 9
<212> TYPE: PRT
<213> ORGANISM: Lama glama

<400> SEQUENCE: 192

Leu Asp Ile Thr Thr Ala Ala Ser Tyr
 1               5

<210> SEQ ID NO 193
<211> LENGTH: 7
<212> TYPE: PRT
<213> ORGANISM: Lama glama

<400> SEQUENCE: 193

Thr Ile Asn Gly Ala Ala Arg
 1               5

<210> SEQ ID NO 194
<211> LENGTH: 12
<212> TYPE: PRT
```

<213> ORGANISM: Lama glama

<400> SEQUENCE: 194

Gly Thr Glu Leu Ala Pro Lys Thr Ala Thr Gly Ala
 1               5                  10

<210> SEQ ID NO 195
<211> LENGTH: 3
<212> TYPE: PRT
<213> ORGANISM: Lama glama

<400> SEQUENCE: 195

Gly Ser Asn
 1

<210> SEQ ID NO 196
<211> LENGTH: 13
<212> TYPE: PRT
<213> ORGANISM: Lama glama

<400> SEQUENCE: 196

Gly Thr Val Leu Ser Val Ala Thr Gly Pro Tyr Gly Tyr
 1               5                  10

<210> SEQ ID NO 197
<211> LENGTH: 9
<212> TYPE: PRT
<213> ORGANISM: Lama glama

<400> SEQUENCE: 197

Trp Gly Ala Gly Glu Asp Glu Asp Tyr
 1               5

<210> SEQ ID NO 198
<211> LENGTH: 12
<212> TYPE: PRT
<213> ORGANISM: Lama glama

<400> SEQUENCE: 198

Lys Ser Arg Asp Ser Ala Gly Leu Ser Trp Asp Tyr
 1               5                  10

<210> SEQ ID NO 199
<211> LENGTH: 11
<212> TYPE: PRT
<213> ORGANISM: Lama glama

<400> SEQUENCE: 199

Leu Val Ala Ser Thr Val Thr Ser Ser Val Ser
 1               5                  10

<210> SEQ ID NO 200
<211> LENGTH: 7
<212> TYPE: PRT
<213> ORGANISM: Lama glama

<400> SEQUENCE: 200

Thr Ile Asn Gly Ala Ala Arg
 1               5

<210> SEQ ID NO 201
<211> LENGTH: 18
<212> TYPE: PRT
<213> ORGANISM: Lama glama

<400> SEQUENCE: 201

```
Gln Thr Arg Pro Arg Pro Tyr Gly Thr Ser Arg Ala Glu Gly Asp Tyr
 1               5                  10                  15

Gly Tyr

<210> SEQ ID NO 202
<211> LENGTH: 30
<212> TYPE: PRT
<213> ORGANISM: Lama glama

<400> SEQUENCE: 202

Asp Val Lys Cys Asp Met Glu Val Ser Cys Pro Asp Gly Tyr Thr Cys
 1               5                  10                  15

Ser Arg Leu Gln Ser Gly Ala Trp Gly Cys Ser Pro Phe Thr
            20                  25                  30

<210> SEQ ID NO 203
<211> LENGTH: 30
<212> TYPE: PRT
<213> ORGANISM: Lama glama

<400> SEQUENCE: 203

Val Val His Cys Asp Met Glu Val Ile Cys Pro Asp Gly Tyr Thr Cys
 1               5                  10                  15

Ser Arg Leu Pro Ser Gly Ala Trp Gly Cys Ser Pro Phe Thr
            20                  25                  30

<210> SEQ ID NO 204
<211> LENGTH: 30
<212> TYPE: PRT
<213> ORGANISM: Lama glama

<400> SEQUENCE: 204

Asp Val Lys Cys Asp Met Glu Val Ser Cys Pro Asp Gly Tyr Thr Cys
 1               5                  10                  15

Ser Arg Leu Pro Ser Gly Ala Trp Gly Cys Ser Pro Phe Thr
            20                  25                  30

<210> SEQ ID NO 205
<211> LENGTH: 15
<212> TYPE: PRT
<213> ORGANISM: Lama glama

<400> SEQUENCE: 205

Ser Met Glu Arg Val Glu Trp Leu Arg Lys Leu Leu Gln Asp Val
 1               5                  10                  15

<210> SEQ ID NO 206
<211> LENGTH: 31
<212> TYPE: PRT
<213> ORGANISM: Lama glama

<400> SEQUENCE: 206

Ser Val Ser Glu Ile Gln Leu Met His Asn Leu Gly Lys His Leu Asn
 1               5                  10                  15

Ser Met Glu Arg Val Glu Trp Leu Arg Lys Leu Leu Gln Asp Val
            20                  25                  30

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Primer
```

```
<400> SEQUENCE: 207
cgccatcaag gtaccagttg a                                              21

<210> SEQ ID NO 208
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 208
gatgtgcagc tgcaggcgtc tggrggagg                                      29

<210> SEQ ID NO 209
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 209
catgaccaca gtgcacagga kgtscagct                                      29

<210> SEQ ID NO 210
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 210
cgattctgcg gccgctgagg agacggtgac ctg                                 33

<210> SEQ ID NO 211
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 211
tatgaagaca ccaggccgat gtgcagctgc aggcg                               35

<210> SEQ ID NO 212
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 212
tatggatcct gaggagacgg tgacctg                                        27
```

SINGLE-DOMAIN ANTIGEN-BINDING ANTIBODY FRAGMENTS DERIVED FROM LLAMA ANTIBODIES

RELATED APPLICATIONS

This application is a divisional of U.S. application Ser. No. 10/031,874, filed Nov. 14, 2002, now abandoned, which is the U.S. National Stage of International Application No. PCT/CA2001/00763, filed May 25, 2001, and claims the benefit under 35 U.S.C. §119(e) of U.S. provisional application Ser. No. 60/207,234, filed May 26, 2000, the disclosures of which are incorporated by reference herein.

FIELD OF THE INVENTION

The invention relates to antigen-binding proteins, in particular to antigen-binding fragments of antibodies derived from a naïve library of llama antibodies and to a phage display library of such fragments. More particularly, the present invention relates to antigen-binding fragments of llama antibodies comprising at least a part of the variable heavy domain (VH or $V_HH$) of antibodies derived from a naïve library of llama antibodies and to a phage display library of such fragments.

BACKGROUND OF THE INVENTION

The immune system in vertebrates provides a defense mechanism against foreign intruders, such as foreign macromolecules or infecting microorganisms. The foreign invaders (antigens), both macromolecules (proteins, polysaccharides, or nucleic acids) and microbes (viruses or bacteria), are recognized through specific binding of the proteins of the host immune system to specific sites on the antigen surface, known as antigenic determinants.

As part of the immune system, B-cells of vertebrate organisms synthesize antigen-recognizing proteins known as antibodies or immunoglobulins (Ig). According to the clonal selection theory, an antigen activates those B-cells of the host organism that have on their surface immunoglobulins that can recognize and bind the antigen. The binding triggers production of a clone of identical B-cells that secrete soluble antigen-binding immunoglobulins into the bloodstream. Antibodies secreted by B-cells bind to foreign material (antigen) to serve as tags or identifiers for such material. Antibody-tagged antigens are then recognized and disposed of by macrophages and other effector cells of the immune system or are directly lysed by a set of nonspecific serum proteins collectively called complement. In this way a small amount of antigen can elicit an amplified and specific immune response that helps to clear the host organism of the source of antigen. Through a complex process of gene splicing combined with additional mutation mechanisms, human B-cells have been estimated to produce a "library" (repertoire) of more than a billion ($10^9$) different antibodies that differ in the composition of their binding sites.

For most vertebrate organisms, including humans and murine species, their antibodies show a common structural pattern which consists of two identical light polypeptide chains and two identical heavy polypeptide chains linked together by disulfide bonds and numerous non-covalent interactions, resulting in a Y-shaped molecule. In humans, there are two different classes (isotypes), λ and κ, of the light chains, with no known functional distinction between them. The heavy chains have five different isotypes that divide immunoglobulins into five different functional classes (IgG, IgM, IgA, IgD, IgE), each with different effector properties in the elimination of antigen.

Of the above five classes, immunoglobulins of the IgG class are the major type in normal serum of humans and many other species and have the four-chain structure shown schematically in FIG. 1. Each chain of an IgG molecule is divided into domains of about 110 amino acid residues, with the light chains having two such domains and the heavy chains having four. Comparison of amino acid sequences between different IgGs shows that the amino-terminal domain of each chain (both light and heavy) is highly variable, whereas the remaining domains have substantially constant sequences. In other words, the light (L) chains of an IgG molecule are built up from one amino-terminal variable domain (VL) and one carboxy-terminal constant domain (CL), and the heavy (H) chains from one amino-terminal variable domain (VH) followed by three constant domains (CH1, CH2, and CH3).

The variable domains are not uniformly variable throughout their length. Three small regions of a variable domain, known as hypervariable regions (loops) or complementarity determining regions (CDR1, CDR2, and CDR3) show much more variability than the rest of the domain. These regions, which vary in size and sequence among various immunoglobulins, determine the specificity of the antigen-antibody interaction. The specificity of an antibody of the type shown in FIG. 1 is determined by the sequence and size of six hypervariable loops (regions), three in the VL domain and three in the VH domain.

By partial digestion with papain, which cleaves the heavy chains in the hinge region, the IgG molecule can be broken down into two identical Fab fragments (Fragment, antigen binding) and one Fc fragment (Fragment, crystallizes easily). Each Fab fragment comprises one complete light chain (consisting of VL and CL domains) linked by a disulfide bridge and noncovalent interactions to a fragment of the heavy chain consisting of VH and CH1 domains. The Fc fragment comprises CH2 and CH3 domains from both heavy chains, also linked by disulfide bridges and noncovalent interactions. The part of the Fab fragment consisting of variable domains of the light and the heavy chain (VL and VH) is known as Fv fragment (Fragment, variable). In an Fv fragment, the variable domains VL and VH are not covalently bound. In an scFv (single chain Fv) fragment, the VL and VH domains are covalently linked by a short peptide linker (spacer), usually 15 to 20 amino acids long, introduced at the genetic level (see FIG. 2).

scFv fragments are recombinant fusion proteins and are produced by techniques of genetic engineering, by expressing in a suitable host, usually in bacteria, a chimeric gene coding for the fragment. Various other recombinant antibody fragments have been designed to substitute for large intact immunoglobulin molecules (see FIG. 2). Other than scFv fragments, these options include Fab or Fv fragments that are stabilized or covalently linked using various strategies (see, for example, Bird et al., *Science*, 242, 423-426 (1988); Huston et al., *Proc. Natl. Acad. Sci. USA*, 85, 5879-5883 (1988); Glockshuber et al., *Biochemistry*, 29, 1362-1376 (1990); Jung et al., *Proteins*, 35-47 (1994); Reiter et al., *Biochemistry*, 5451-5459, 18327-18331 (1994); Young et al., *FEBS Lett.*, 135-139 (1995)). Small antigen-binding fragments of natural antibodies are advantageous for medical applications, for example cancer targeting and imaging, when small antigen-biding molecules are required to penetrate into solid tumors.

Recent advances in gene technology have greatly facilitated the genetic manipulation, production, identification and conjugation of recombinant antibody fragments and broadened the potential utility of antibodies as diagnostic and therapeutic agents. Of particular importance to such applications is the possibility to alter the fine specificity of the antibody binding site, to create small stable antigen-binding fragments, to prepare fusion proteins combining antigen-binding domains with proteins having desired therapeutic properties, for the purpose of immunotargeting, or to "humanize" antibodies of other species, for example murine antibodies (see FIG. 2).

The genetic engineering has also made possible to screen in vitro for antibodies having a predetermined binding specificity. This may be achieved by constructing first a gene library of antibodies or antibody fragments, for example by polymerase chain reaction (PCR)-amplification of cDNA derived from B-lymphocytes using suitable primers, or by in vitro gene synthesis. The gene library may contain sequences corresponding to certain fragments of natural antibodies, or randomized antigen-binding regions, or new combinations of heavy/light chains, thus creating the potential for generating antibodies which could never be obtained from natural sources, for example, antibodies to highly toxic substances or antigens tolerated by the human immune system. By random or designed mutations, the affinity or specificity of the antigen binding can be manipulated, for example, to reach affinities never observed with natural antibodies.

To screen a gene library, which may contain many millions or even billions of different clones, for genes of antibodies having the desired binding specificity, a selection system comparable to that of the immune system is required. Such a selection system can be achieved by inserting the library genes into the genome of microorganisms capable of displaying on their surface the antibody corresponding to the inserted gene, in analogy to the expression of an immunoglobulin antigen receptor on the surface of a B-cell. Microorganisms most frequently used for providing such a display are filamentous bacteriophages, such as fd or M13 phages (phage display). The collection of phage particles having inserted genes of a library of proteins, such as antibodies, and displaying these proteins on the particles' surface is known as a phage display library. The display of the library of antibodies on the surface of phage particles provides a physical link between the antigen-binding function of an antibody and the antibody gene. Using the affinity to a preselected antigen, the whole organism (phage) displaying this affinity can be identified and separated out of billions of non-specific clones, usually through binding to the antigen immobilized on a support, technique usually referred to as panning (see, for example, Scott et al., *Science,* 249, 386-390 (1990); Winter et al., *Annual Rev. Immunology,* 12, 433-455 (1994)). Phage clones binding to the antigen can be then amplified and used to produce the specific antibody or antibody fragment in *E. coli* or in other suitable organism.

For naturally occurring antibodies, there are examples that whole heavy chains alone retain a significant binding ability in the absence of light chains. It is also well established, from structural studies, that the CDR3 of the heavy variable domain generally contributes the most to antigen binding, because CDR3 amino acid residues are responsible for most of the surface contact area and molecular interaction with the antigen (Padlan, E. A., *Mol. Immunology,* 31, 169-217 (1984); Chothia et al., *J. Mol. Biol.,* 196, 904-917 (1987); Chothia et al., *J. Mol. Biol.,* 186, 651-663 (1985)). Less binding activity was observed for light chain. In view of these findings, attempts were made to isolate single VH domains. For example, VH domains were isolated from expression libraries derived from immunized mice (Ward et al., *Nature,* 341, 544-546 (1989)). In another report, antigen-binding VH domains were rescued from an antibody phage library that was made from a vaccinated patient (Cai et al., *Proc Natl. Acad. Sci. USA,* 93, 6280-6285 (1996)). Antigen-binding antibody fragments consisting of a single VH domain, known as dAbs or sdAbs (single-domain antibodies), are becoming an attractive alternative to single chain Fv (scFv) fragments. Despite smaller binding surface, their demonstrated affinity is comparable to that demonstrated by scFv fragments (Davies et al., *Biotech.,* 13, 475-479 (1995)). Because of their smaller size, being half of the size of scFvs, sdAbs are amenable to detailed NMR structural studies (Davies et al., *FEBS Letters,* 339, 285-290 (1994)). Additionally, due to their simpler structure, sdAbs are more stable and have simpler folding properties.

Recently, a new class of antibodies known as heavy chain antibodies (HCA, also referred to as two-chain or two-chain heavy chain antibodies) have been reported in camelids (Hamers-Casterman et al., *Nature,* 363, 446448 (1993); see also U.S. Pat. No. 5,759,808; U.S. Pat. No. 5,800,988; U.S. Pat. No. 5,840,526; and U.S. Pat. No. 5,874,541). Compared with conventional four-chain immunoglobulins of IgG-type, which are also produced by camelids, these antibodies lack the light chains and CH1 domains of conventional immunoglobulins. One of the salient features of these naturally occurring heavy chain antibodies is the predominant presence of Glu, Arg and Gly at VL interface positions 44, 45 and 47 (Kabat numbering), respectively, of their variable domain (designated $V_HH$). The same positions in the variable domain of the heavy chain of conventional four-chain antibodies (designated VH) are almost exclusively occupied by Gly, Leu and Trp. These differences are thought to be responsible for the high solubility and stability of camelid HCA variable domain ($V_HH$), as compared with the relative insolubility of VH domain of the conventional four-chain antibodies. Two more salient features of camelid $V_HH$ domains are their comparatively longer CDR3 and high incidence of cysteine pairs in CDRs. It appears that cysteine pairs mediate the formation of a disulfide bridge and are therefore involved in modulating the surface topology of the antibody combining site. In the crystal structure of a camel sdAb-lysozyme complex, a rigid loop protruding from the sdAb and partly stabilized by a CDR disulfide linkage extends out of the combining site and penetrates deeply into the lysozyme active site (Desmyter et al., *Nature Struct. Biol.,* 3, 803-811 (1996)).

More recently, a number of camelid sdAbs phage display libraries have been generated from the $V_HH$ repertoire of camelids immunized with various antigens (Arbabi et al., *FEBS Letters,* 414, 521-526 (1997); Lauwereys et al., *EMBO J.,* 17, 3512-3520 (1998); Decanniere et al., *Structure,* 7, 361-370 (1999)). By creating polyclonal libraries, many highly soluble sdAbs with high affinity and specificity have been isolated. However, it has been questioned whether sdAbs with desired affinity and defined conformations can be generated in the absence of prior immunization, i.e., with a naïve library (Lauwereys et al., supra). Immunization of domesticated valuable animals, such as camelids, raises serious ethical implications related to experiments with animals. Moreover, this approach has serious drawbacks because most of the pathogenic antigens cannot be injected into camelids, as this could endanger their lives. Considering the above drawbacks and limitations of the prior art, there exists a strong need for the generation of phage display libraries of sdAb antibody fragments derived from naïve libraries of camelid antibodies, in particular sdAb fragments of camelid heavy chain antibodies, which libraries may become a universal source of sdAbs for in vitro selection against any antigen of interest as a target.

SUMMARY OF THE INVENTION

The present invention has overcome the above-discussed prior art limitations by generating a large size (in the order of $10^9$) phage display library of antibody fragments of a non-immunized llama, which fragments comprise at least a part of the variable heavy domain (VH or $V_HH$ domain) of llama antibodies. In a preferred embodiment, the fragments consist essentially of the variable heavy domain (VH or $V_HH$ of llama antibodies (sdAb fragments). This library possesses a number of unique features which distinguish it from similar libraries generated from other camelids. The large size of the library considerably increases the probability of isolating therefrom antigen-binding fragments having high affinity to almost any predetermined target (antigen) of interest. This has been demonstrated by isolating from the library fragments binding specifically to several preselected antigens as targets.

Thus, according to one aspect, the invention provides a phage display library of antigen-binding fragments of llama antibodies, said fragments comprising at least a part of the variable heavy domain (VH or $V_HH$) of the antibodies. Preferably, the antigen-binding fragments consist of a complete variable heavy domain (VH or $V_HH$) of the antibodies (sdAb fragments)

According to another aspect, the invention provides an antigen-binding fragment of a llama antibody, said fragment comprising at least a part of the variable heavy domain (VH or $V_HH$) of the antibody. Preferably, the antigen-binding fragment consists of a complete variable heavy domain (VH or $V_HH$) of the antibody (sdAb fragment).

According to yet another aspect, the invention provides a cDNA library comprising nucleotide sequences coding for antigen-binding fragments of llama antibodies, said library obtained by isolating lymphocytes from a biological sample obtained from a non-immunized llama; isolating total RNA from the lymphocytes; reverse-transcribing and amplifying RNA sequences coding for the antigen-binding fragments; cloning the amplified cDNA in a vector; and recovering the obtained clones. Preferably, the antigen-binding fragments consist of a complete variable domain (VH or $V_HH$) of the antibodies (sdAb fragment) and the cloning vector is a filamentous bacteriophage.

According to yet another aspect, the invention provides a process for the preparation of an antigen-binding fragment of a llama antibody, said fragment binding to a predetermined antigen, said process comprising the steps of isolating lymphocytes from a biological sample obtained from a non-immunized llama; isolating total RNA from the lymphocytes; reverse-transcribing and amplifying RNA sequences coding for antigen-binding fragments; cloning the cDNA sequences so obtained into a first vector, said first vector capable of a surface display of the corresponding antigen-binding fragments; subjecting the clones to antigen affinity selection and recovering clones having the desired affinity; for the recovered clones, amplifying DNA sequences coding for antigen-binding fragments; cloning the amplified DNA sequences into a second vector; transforming prokaryotic cells with the second vector under conditions allowing expression of DNA coding for antigen-binding fragments; and recovering the antibody fragments having the desired specificity.

Other advantages, objects and features of the present invention will be readily apparent to those skilled in the art from the following detailed description of preferred embodiments in conjunction with the accompanying drawings and claims.

DETAILED DESCRIPTION OF THE PREFERRED EMBODIMENTS

Figure 1:
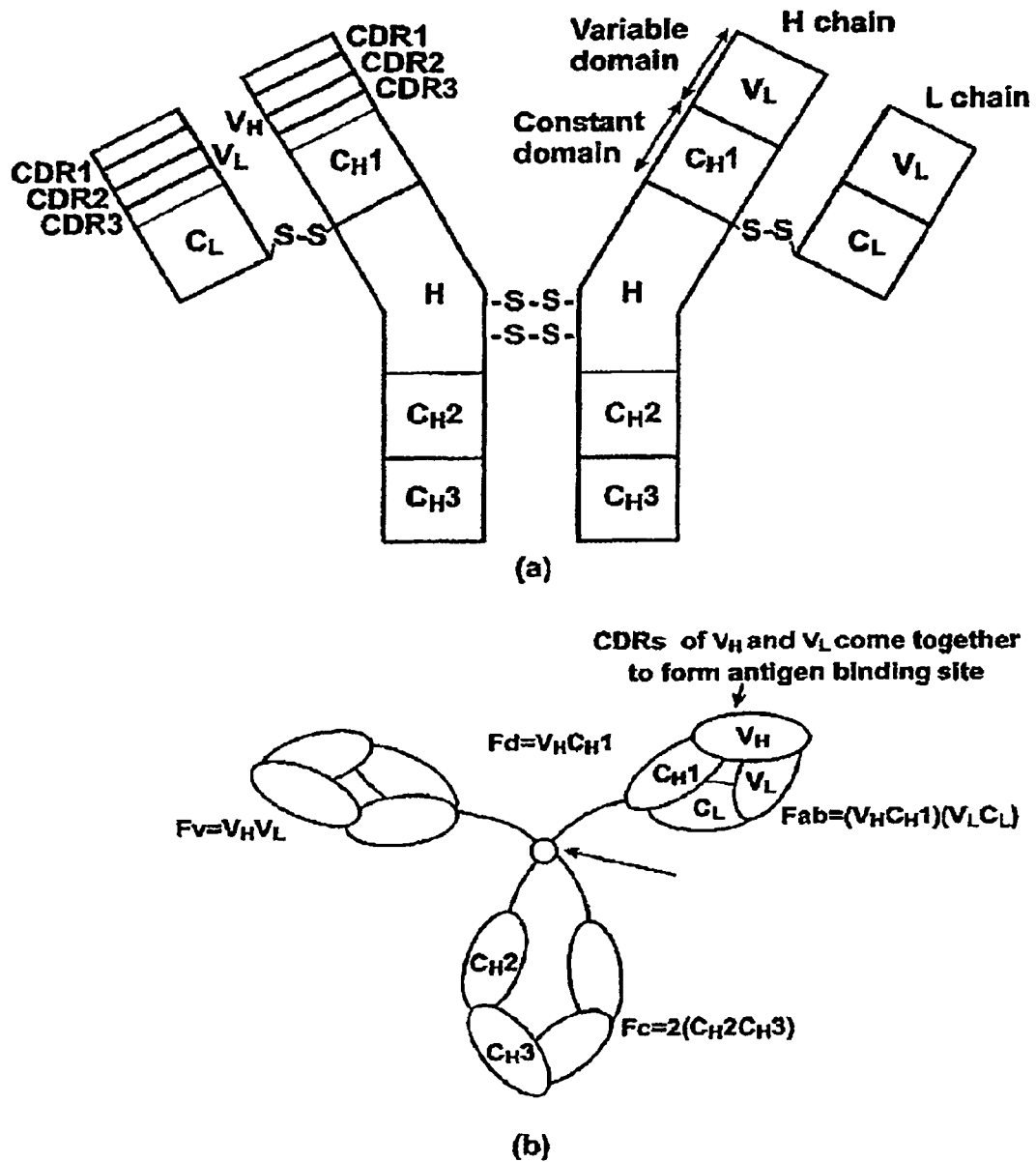
FIG. 1 is a schematic representation of a typical four-chain IgG-type immunoglobulin (antibody) showing (a) the structure and arrangement of heavy and light chains and the approximate positioning of interchain disulfide bonds, and (b) the organization of the antibody molecule into paired domains.
Figure 2:
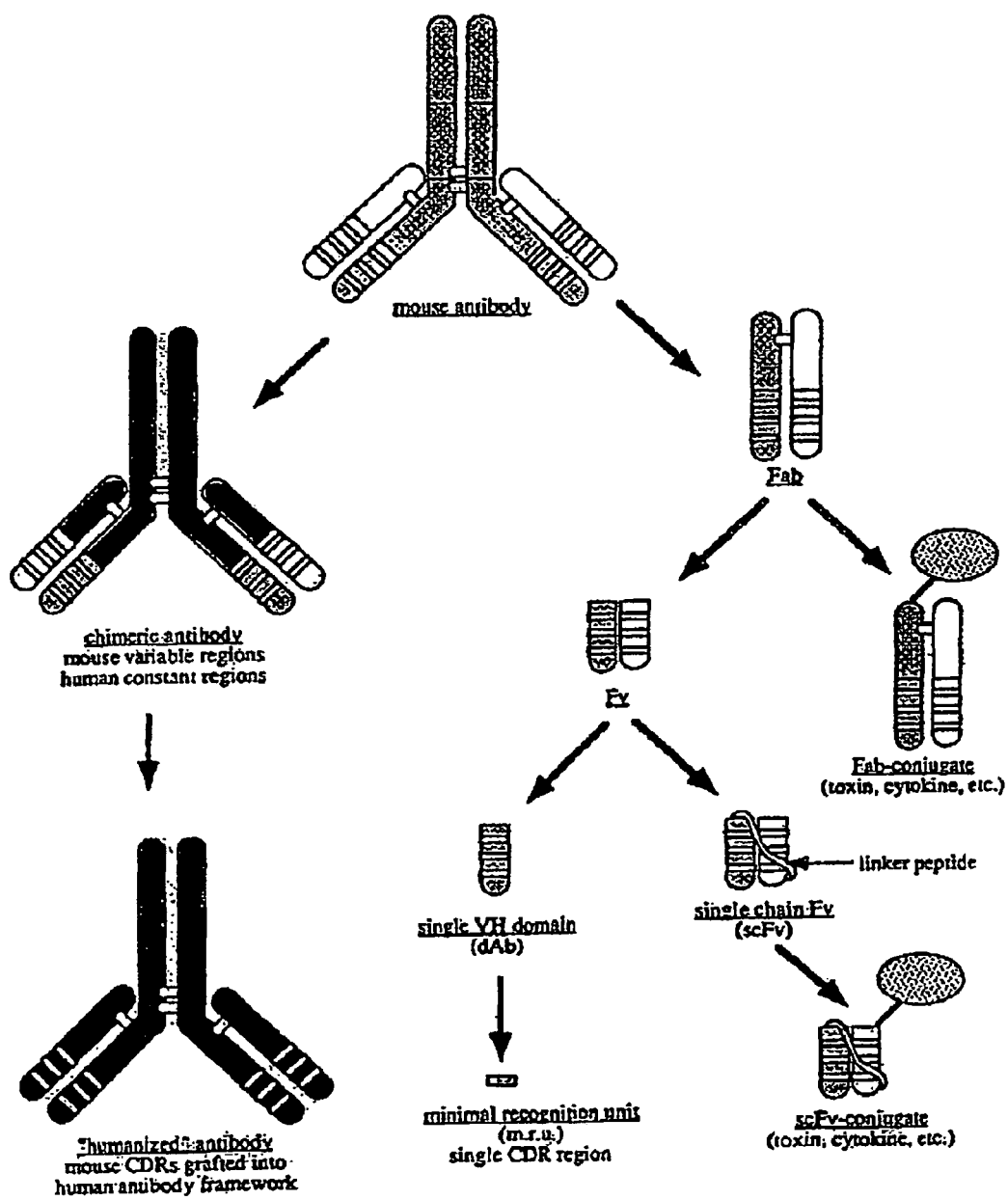
FIG. 2 is a schematic representation of various modifications and fragments of IgG-type antibodies, and antigen-binding fusion proteins derived from such fragments.

In the following, positions of amino acid residues in antibodies and antibody fragments are indicated according to the Kabat numbering.

The present invention provides a large size (in the order of $10^9$) phage display library of single-domain fragments of variable heavy domains (VH and $V_HH$) of llama antibodies. The library, which has been generated using lymphocytes of a non-immunized animal (naïve library), can be used for in vitro selection against any antigen of interest as a target. The size of the library makes it highly probable that an antibody specific to the target will be identified among the library's sdAb fragments. This utility of the library has been demonstrated by isolating therefrom sdAbs binding specifically to various preselected antigens as targets.

The choice of a naïve library as the source of llama antibodies was based in part on the fact that the immune system of camelids has evolved over time in harsh environments and that its unique physiological and morphological features have helped the camelids to withstand water scarcity, adapt to climate extremes and develop a natural resistance to deadly viral diseases. The sero-epidemiological studies have confirmed that camelids produce antibodies to a great number of pathogenic viruses without developing the disease (Werney et al., Infectious Diseases of Camelids, Blackwell's Wissenschaft Verlag, Berlin (1995)). This means that antibodies of therapeutic importance can be isolated from the antibody repertoire of camelids without prior immunization with potentially dangerous pathogens or fragments thereof.

Another advantage of choosing a naïve library as the source of llama antibodies concerns anti-idiotypic antibodies. An anti-idiotypic antibody (a second antibody) recognizes the idiotope of another antibody (a first antibody) as an antigen, meaning that the first antibody recognizes in turn the second (anti-idiotypic) antibody as its antigen. Anti-idiotypic antibodies have gained a widespread clinical use, e.g., in vaccine development for cancer and cholera [Grant, S. C., Kris, M. G., Houghton, A. N., and Chapman, P. B., 1999; Herlyn, D. and Birebent, B., 1999]; [Maxwell-Armstrong, C. A., Durrant, L. G., and Scholefield, J. H., 1998]; [Pierre, P. G., Lucas, G., Van Damme, M., and Vaerman, J. P., 1992]) and in autoimmune disease therapy [Perosa, F., Scudeletti, M., Imro, M. A., Dammacco, F., Luccarelli, G., and Indiveri, F., 1997]). They have also been shown to increase the protective immune response against parasites, bacteria and viruses [Feodorova, V. A., Devdariani, Z. L., and Nazarova, L. S., 1999]) and references therein). Since the original antigens (i.e., cancer, bacterial or viral antigens) may have been weakly- or non-immunogenic or toxic to the cells, anti-idiotypic antibodies have been used in their place to provide immune protection against diseases. However, in almost all cases reported to date, anti-idiotypic antibodies have been developed by immunization. The present invention eliminates the step of immunization and allows isolation of anti-idiotypic antibodies of potential diagnostic and therapeutic value from a naïve library.

Among the camelids, llama is the smallest animal which can survive in a severe, cold climate. Lymphocytes of a llama from a farm located in Osgoode (Canada) have been used to generate the phage display library of variable heavy domains of llama antibodies. From this library, sdAbs binding specifically to several preselected antigens have been subsequently isolated and characterized.

Construction of a Naïve LLAMA sdAb Phage Display Library

Figure 3:
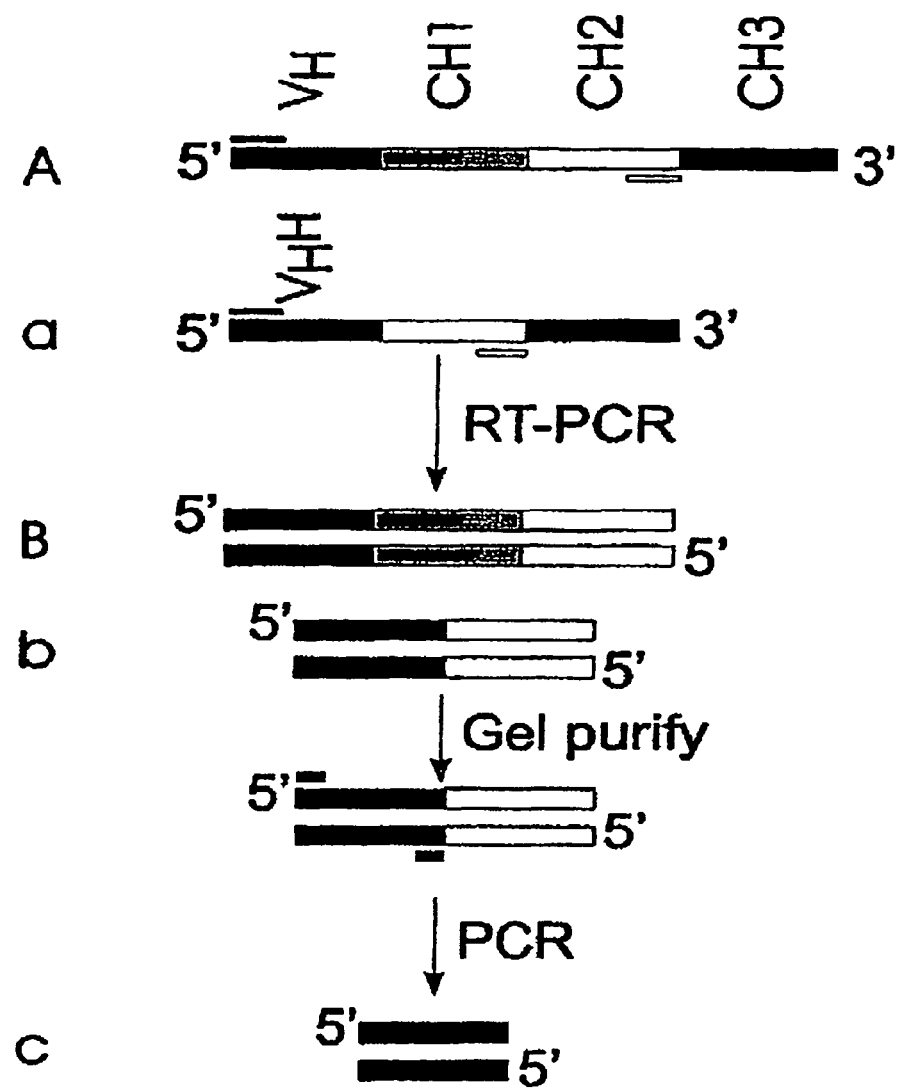
FIG. 3 is a schematic representation of steps involved in construction of the phage display library of llama sdAb antibody fragments according to the present invention. For simplicity, only the coding sequences of the mRNA transcripts are shown. A, a: heavy chain mRNA of conventional four-chain (A) and two-chain heavy chain (a) antibodies; B, b: RT-PCR product derived from A and a, respectively; c: $V_HH$ derived from heavy chain antibodies. Variable (VH) and constant (CH) domains are marked with dark and light shading, respectively.

FIG. 3 depicts a schematic representation of steps involved in the construction of the $V_HH$-derived sdAb phage display library. As the first step, lymphocytes from the fresh blood of llama (from a farm located at Osgoode, Ontario, Canada) were prepared and their RNA was isolated using techniques well known to those skilled in the art. RT-PCRs (reverse transcriptase-polymerase chain reactions) were performed using primers annealing at the 5' end of VH or $V_HH$ and CH2 genes of IgG. The amplified products were separated and fragments of the expected size derived from conventional IgG (~900 bp) and heavy chain IgG (~600 bp) were observed on the agarose gel. The smaller fragment was gel purified and used in a second PCR to amplify the $V_HH$ genes. The amplification products were cloned into fd-tet (GIIID) vector, between the leader signal and gene III, to produce fusion proteins, which were displayed on the filamentous phage particles using a modified procedure.

As is well known to those skilled in the art, the probability of isolating a protein with high affinity or specificity against a target (antibody) of interest increases with the size of the library. Generally, two different types of vectors are used for generating phage display libraries: phagemid vectors and phage vectors. Libraries having size in the order of $10^8$ can be constructed with relative ease using phagemid vectors. However, a phagemid-based libraries suffers from some serious drawbacks. First, phagemid vectors provide typically a monovalent display and therefore may not select for lower binding (of lower affinity), but potentially important antibody fragments. Second, a phagemid-based library allows for the enrichment of phage particles displaying deleted versions of the antibody fragments. Such particles, often with no binding activity, are preferably selected during the panning process over those displaying the full-length fragments and therefore obscure the process of selection of the full-length binders. Third, constructing a phagemid-based library requires a helper phage and therefore library construction, panning and downstream phage binding assays become a far more complicated and tedious task. For these reasons the use a phage vector for the library construction is preferred.

One of the most widely used phage vectors is fd-tet (Zacher III et al., Gene, 9, 127-140 (1980)) which consists of fd-phage genome, plus a segment of Tn10 inserted near the phage genome origin of replication. Tn10 contains a tetracycline resistance gene, tetA, and thus confers tetracycline resistance to the host cells carrying the fd-tet vector. It has often been observed that the size of the fd-tet based library was generally low (in the range of $10^5$-$10^6$) (Harrison et al., Methods in Enzymology [Ed. Abelson, J. N.], 267, 83-109 (1996); Krebber et al., FEBS Letters, 377, 227-231 (1995)), possibly due to the toxic effect of teta gene product on the host cells. According to the modified procedure of the present invention, the library was propagated as plaques in the absence of tetracycline, resulting in a llama $V_HH$ library of size of approximately $8.8 \times 10^8$. This is the largest size library ever obtained using fd-tet vector. Due to its size, the library has an enhanced probability of selecting therefrom proteins (antibody fragments) binding to almost any given target (antigen).

It would be known to those skilled in the art that, at least in principle, the display library of the invention could be generated using vectors other than phages, such as bacteria (e.g., E. coli) ([Daugherty, P. S., Olsen, M. J., Iverson, B. L., and Georgiou, G., 1999; Georgiou, G., Stathopoulos, C., Daugherty, P. S., Nayak, A. R., Iverson, B. L., and Curtiss, R., III, 1997])) or yeast (e.g., Saccharomyces cerevisiae) ([Kieke, M. C., Shusta, E. V., Boder, E. T., Teyton, L., Wittrup, K. D., and Kranz, D. M., 1999; Kieke, M. C., Cho, B. K., Boder, E. T., Kranz, D. M., and Wittrup, K. D., 1997; Cho, B. K., Kieke, M. C., Boder, E. T., Wittrup, K. D., and Kranz, D. M., 1998; Boder, E. T. and Wittrup, K. D., 1997])). Obtaining large libraries, comparable in size to phage display libraries, is, at least in theory, possible using these vectors. However, these display systems have not been of a widespread use, as they require expensive flow cytometry cell sorting instruments for selection. In addition, the E. coli display system is not suitable for panning against large macromolecules, such as proteins, due to the interference of the lipopolysaccharide layer of E. coli with the binding process ([Boder, E. T. and Wittrup, K. D., 1997]supra). Surface display of an scFv on mammalian cells has also been reported [Rode, H. J., Moebius, U., and Little, M., 1999]); [Rode, H. J., Little, M., Fuchs, P., Dorsam, H., Schooltink, H., de Ines, C., Dubel, S., and Breitling, F., 1996])). However, no antibody library has been so far constructed using vectors other than phages, as the construction and screening in these alternative display systems are not as rapid or versatile as for phage display libraries.

Sequence Analysis

Figure 4:
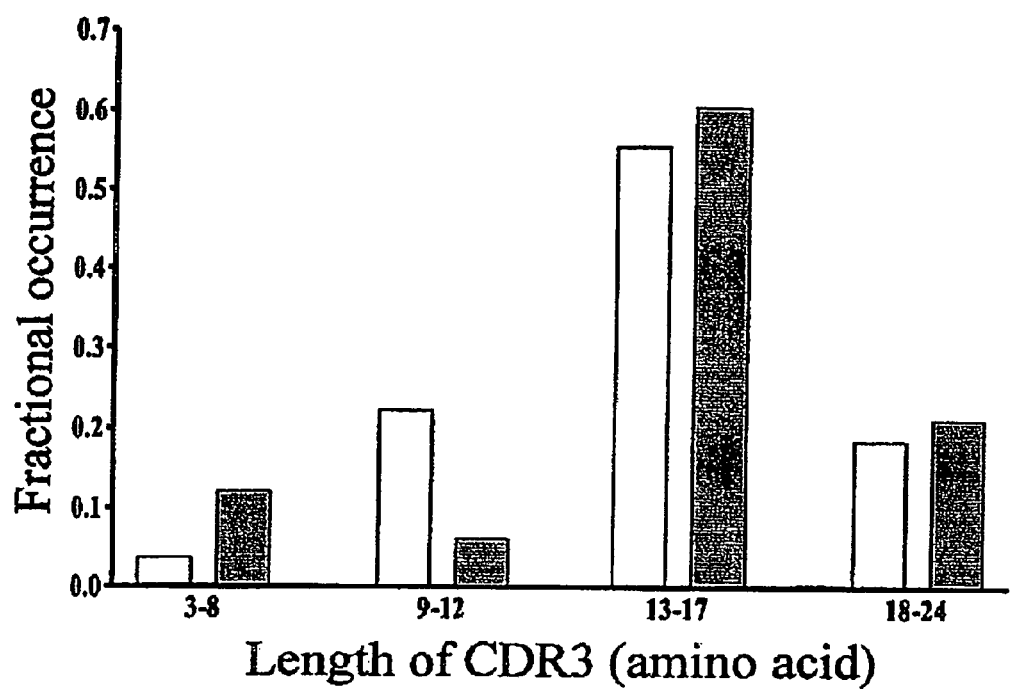
FIG. 4 is a bar graph showing fractional occurrence of the CDR3 lengths. Gray bars represent data according to the present invention, whereas the white bars represent the published data for llama $V_HH$ (Vu et al., *Mol. Immunol.*, 34, 1121-1131 (1997)).

Colony PCR of 80 randomly selected clones showed that more than 60% had the full-length $V_HH$ genes (sdAbs). The identity of the VL interface amino acids at position 44, 45 and 47 as well as the CDRs sequence of 28 randomly selected sdAbs have been determined and are summarized in Table 1. FIG. 4 shows the fractional occurrence of the CDR3 length. For comparison, previously published sequence data obtained from llama HCAs are also included. Similar to the previous results, the majority of the CDRs of the sequenced sdAbs are 13-17 amino acid long, demonstrating that the llama sdAb library of the invention is derived from heavy chain antibodies. However, the present library is distinct in several aspects from the known $V_HH$ libraries.

TABLE 1

CDR/H1 sequences of 28 randomly selected dAbs from the llama library. The VL interface residues at positions 37, 44, 45 and 47 are also included. Position 35 is in each case the last residue in CDR/H1 sequence.

| sdAb | 37 | 44 | 45 | 47 | CDR1/H1 | | CDR2 | | CDR3 | |
|---|---|---|---|---|---|---|---|---|---|---|
| C1 | V | G | L | W | GFTFSSYYMS | SEQ ID NO: 1 | GIYSDSSITAYADSVKG | SEQ ID NO: 29 | MVMGPAATGYEY | SEQ ID NO: 57 |
| C2 | F | E | R | F | GRTFSNYHMG | SEQ ID NO: 2 | SIKWSGGNTYYADSVKG | SEQ ID NO: 30 | GSKYGGSWSRSQDAYNY | SEQ ID NO: 58 |
| C4 | F | E | R | F | GRIFSNAAMG | SEQ ID NO: 3 | AIRWSDGNTYYADSVKG | SEQ ID NO: 31 | GIGTFGSSWTRADRYRY | SEQ ID NO: 59 |
| C5 | Y | Q | R | L | RSIFSINTLG | SEQ ID NO: 4 | WITSGGATYYADSMKG | SEQ ID NO: 32 | RVPLDY | SEQ ID NO: 60 |
| C7 | F | E | R | F | GRSFSTYRVG | SEQ ID NO: 5 | GINWNGVKTRYSDSMND | SEQ ID NO: 33 | DQRFDGDDWSPSAFTR | SEQ ID NO: 61 |
| C8 | F | E | R | F | GNTISGYATG | SEQ ID NO: 6 | AVTWSGYSVVYAKSPKG | SEQ ID NO: 34 | VFVRTAGVPTLGEYDY | SEQ ID NO: 62 |
| C9 | F | G | R | F | GGSFSNYNMG | SEQ ID NO: 7 | GIGWSGGRIIVADSVKG | SEQ ID NO: 35 | TKQFFPLSN?SVWYDY | SEQ ID NO: 63 |
| C12 | W | K | R | F | GRIPRNYPIG | SEQ ID NO: 8 | GISWTSGTTYFADSVKG | SEQ ID NO: 36 | SERDFYTRNYFTFESLYDY | SEQ ID NO: 64 |
| C15 | F | A | R | F | GESIASFNLG | SEQ ID NO: 9 | AVSRTGETTDYADAVKG | SEQ ID NO: 37 | DYNLGTFVTRKDSMYDF | SEQ ID NO: 65 |
| C16 | F | E | R | F | GRTFSSVSMG | SEQ ID NO: 10 | AINWRGVSTYYADSVKG | SEQ ID NO: 38 | RRNFFGNNSAGQYAY | SEQ ID NO: 66 |
| C17 | L | E | R | I | GLTFGDYAMG | SEQ ID NO: 11 | TISRIGSTTYYADSVKG | SEQ ID NO: 39 | SRYVLKYDKDAY | SEQ ID NO: 67 |
| C22 | F | E | R | F | GRTFSSVTMG | SEQ ID NO: 12 | AMTRNSGSTYYADSVKG | SEQ ID NO: 40 | KASMYGSTLYPPTGYNY | SEQ ID NO: 68 |
| C24 | F | E | R | F | GRTFSRFAMG | SEQ ID NO: 13 | AISWSGGTTYGADSAKG | SEQ ID NO: 41 | GRAVSDYDY | SEQ ID NO: 69 |
| C25 | Y | E | R | L | GSIFSESAMG | SEQ ID NO: 14 | AITLDGRTNYAYYAEG | SEQ ID NO: 42 | LRSRAVMDTIPNY | SEQ ID NO: 70 |
| C26 | F | E | R | F | GRTFSSDAMG | SEQ ID NO: 15 | AISWSGGSTYYADSVKG | SEQ ID NO: 43 | DRRRYYSGSYPPSEYDY | SEQ ID NO: 71 |
| C29 | V | G | L | W | GFTFSNFWMG | SEQ ID NO: 16 | QINTGGDITTYSDSVKG | SEQ ID NO: 44 | ARSVPLSDPRTYSS | SEQ ID NO: 72 |
| C30 | L | E | R | V | GRSFNHYIMG | SEQ ID NO: 17 | SIDWNSGRTNYADSVKG | SEQ ID NO: 45 | AAAASTLVGGSYDY | SEQ ID NO: 73 |
| C31 | Y | E | R | F | GLPFSTYSMG | SEQ ID NO: 18 | VIGGGGNTYHAADSLKD | SEQ ID NO: 46 | DRDFTIVAGFIRSQYSPRAVEY | SEQ ID NO: 74 |
| C33 | F | E | R | F | GRTFSTYTMG | SEQ ID NO: 19 | AISRNSVGTYYRDSVKG | SEQ ID NO: 47 | DPMYGRSVMSTRYNY | SEQ ID NO: 75 |

TABLE 1-continued

CDR/H1 sequences of 28 randomly selected dAbs from the llama library. The VL interface residues at positions 37, 44, 45 and 47 are also included. Position 35 is in each case the last residue in CDR/H1 sequence.

| sdAb | 37 | 44 | 45 | 47 | CDR1/H1 | | CDR2 | | CDR3 | |
|------|----|----|----|----|---------|---|------|---|------|---|
| C34 | F | D | R | F | GYTFSSHAMG | SEQ ID NO: 20 | AISASGGNQYYKYFAKG | SEQ ID NO: 48 | ATKQFSNAYSDYVHDYDY | SEQ ID NO: 76 |
| C35 | F | E | R | G | GFRFAEYAIG | SEQ ID NO: 21 | YISTSDKTTYYSDFAEG | SEQ ID NO: 49 | GLYYSDYRTPEYTEYVH | SEQ ID NO: 77 |
| C40 | F | E | R | F | GRTFSRFAMG | SEQ ID NO: 22 | AISWSGGTAYGADSAKG | SEQ ID NO: 50 | GRAVSDYDY | SEQ ID NO: 78 |
| C43 | V | G | L | W | GFTFVDYSMT | SEQ ID NO: 23 | AINWNGRLTYYAESMKG | SEQ ID NO: 51 | GELYGMGSKHDY | SEQ ID NO: 79 |
| C44 | V | G | L | W | GFTFSNYYMY | SEQ ID NO: 24 | MVNTGGGGTRYADSVRG | SEQ ID NO: 52 | DRPQSGWSMDY | SEQ ID NO: 80 |
| C45 | F | E | R | F | GLTFSSYVMG | SEQ ID NO: 25 | AIITSGRSTYYADSVKG | SEQ ID NO: 53 | TKWVRRPADYNY | SEQ ID NO: 81 |
| C46 | F | E | R | F | GGTFTDYAMG | SEQ ID NO: 26 | AINWGGYSTYYSDAVKG | SEQ ID NO: 54 | DPQLITTPEYNY | SEQ ID NO: 82 |
| C48 | V | G | L | W | GFTFSNYYMY | SEQ ID NO: 27 | MVNTGGGGTRYADSVRG | SEQ ID NO: 55 | DRPQSGWSMDY | SEQ ID NO: 83 |
| C49 | F | E | R | F | GNTISDYATG | SEQ ID NO: 28 | SIGRRTGWQVYSDSVKG | SEQ ID NO: 56 | SQDSGFDTPVTESHLYGY | SEQ ID NO: 84 |

Previously generated camelid sdAb libraries were characterized by typical presence of Glu, Arg and Gly in positions 44, 45 and 47, respectively, of the VL interface of $V_H$H domain. The occurrence of cysteine at position 45 was also frequent in $V_H$H, as opposed to VH domain of four-chain IgGs. The present library, as shown by sequence analysis (Table 1), lacks these characteristics, as only one sdAb (C35) has Glu44, Arg45 and Gly47. The majority of sdAbs of the present library have Arg in position 45 of the VL interface. This occurrence of Arg45 is not unique to camelid $V_H$H, as a number of conventional antibodies, such as H1-I6 (VH) and V13 (VH), have been found to have Arg in position 45 (Blier et al., *J. Immunol.*, 139, 39964006 (1987); Crews et al., *Cell*, 29, 59-66 (1981)). The presence of Gly at position 35 was observed to always accompany Phe at position 37, unlike a previously reported llama library in which this pairing was observed in only 50% of the sequences. This is noteworthy in view of the fact that Gly at position 35 results in local conformational changes that allow Trp101 to stack with Arg45 in addition to engaging in aromatic-aromatic interactions involving Phe37 and Trp103. For the present library, 12 of 27 sdAbs have Trp at position 52a, whereas only 1 of the 51 previously published sequences have Trp at this position.

Another major difference between the present library and the previously reported $V_H$H libraries of camelids concerns the CDR cysteins. Previously generated libraries were characterized by a high incidence of cysteine pairs in CDRs, whereas none of the 28 sdAbs (Table 1) of the present library had any cysteine in their CDRs. The library of the invention is therefore characterized by a very low presence or by the absence of cysteine residues in CDRs.

Finally, the present library, which was designed and constructed to contain only antibody fragments consisting of variable heavy chain domains ($V_H$Hs), also contains a substantial number of typical conventional variable heavy domains (VHs) (for example, sdAbs C1, C29, C43, C44 and C48 of Table 1, some sdAbs of Table 2). This contamination is most likely the results of PCR cross-overs between the VHs and $V_H$Hs during the step of RT-PCR (FIG. 3) (Tomlinson et al., *J. Mol. Biol.*, 227, 776-798 (1992); Muyldermans et al., *Protein Eng.*, 7, 1129-1135 (1994)). These VHs are genuine antigen binding fragments, as shown in Table 2, produced in high yield in *Escherichia coli*. They are highly soluble, have excellent temperature stability profiles and do not display any aggregation tendencies (Tanha et al., manuscript in preparation; Vranken et al., submitted). The very close similarity of these molecules to human VHs makes them potentially very useful as therapeutic sdAbs.

For the library of the invention, amino acids of the VL interface are most frequently:
- at position 44 - Gly, Glu, Gln, Lys, Ala and Asp,
- at position 47 - Leu, Phe, Pro, and Arg, and
- at position 47 - Trp, Tyr, Phe, Leu, Ile, Val and Gly.

For the library of the invention, CDRs can be selected from the following sequences:

| | | |
|---|---|---|
| CDR1/H1: | GFTFSSYAMS | (SEQ ID NO: 85) |
| | GFTFSSYYMS | (SEQ ID NO: 86) |
| | GFTFDEHAIG | (SEQ ID NO: 87) |
| | GFTVSSNHMT | (SEQ ID NO: 88) |
| | GFTFSSYHMA | (SEQ ID NO: 89) |
| | GFTFSRHQMS | (SEQ ID NO: 91) |
| | GFTFRTYYMN | (SEQ ID NO: 92) |
| | GFIFSSYAMS | (SEQ ID NO: 93) |
| | GFTFSTYAMT | (SEQ ID NO: 95) |
| | GFTFSGYAMS | (SEQ ID NO: 99) |
| | GFAFSNYRMT | (SEQ ID NO: 100) |
| | GFTFSRYAMS | (SEQ ID NO: 101) |
| CDR2: | GIEGGGITRYADSVKG | (SEQ ID NO: 102) |
| | TIKPGGGSTYYADSVKG | (SEQ ID NO: 103) |
| | TIDIGGGRTYADSVKG | (SEQ ID NO: 104) |
| | RISSDGRNTYYADSVKG | (SEQ ID NO: 105) |
| | TINPGDGSTYYADSVKG | (SEQ ID NO: 106) |
| | HIDTGGSTWYAASVKG | (SEQ ID NO: 107) |
| | TINIDGSSTYYADSVRG | (SEQ ID NO: 109) |
| | GINSFGGSKYYADSVKG | (SEQ ID NO: 110) |
| | TINTSGRGTYYADSVKG | (SEQ ID NO: 112) |
| | AINSGGGSTSYADSVKG | (SEQ ID NO: 113) |
| | HIDTGGGSTWYAASVKG | (SEQ ID NO: 114) |
| | DINSGGDSTRNADSVKG | (SEQ ID NO: 115) |
| | SINSGGGSTYYADSVKG | (SEQ ID NO: 116) |
| | RINSIGDRISYADSVKG | (SEQ ID NO: 117) |
| CDR3: | AHGGYGAFGS | (SEQ ID NO: 119) |
| | YSGGALDA | (SEQ ID NO: 122) |
| | LSQGAMDY | (SEQ ID NO: 124) |
| | IDRERAFTS | (SEQ ID NO: 127) |
| | IDWERAFTS | (SEQ ID NO: 128) |
| | QGYAGSYDY | (SEQ ID NO: 129) |
| | LGVPGTFDY | (SEQ ID NO: 130) |
| | TNRGIFDY | (SEQ ID NO: 131) |
| | TPGSSGVYEY | (SEQ ID NO: 132) |
| | TQTGSHDY | (SEQ ID NO: 133) |
| | QVGTAYDY | (SEQ ID NO: 134) |
| | RRGSSGVYEY | (SEQ ID NO: 135) |

Selection Against Antibody Antigens

Special cases of antibody-antigen reactions are those in which the antigen (Ag) is itself an antibody (Ab), as discussed above. Single domain anti-idioptypic (anti-Id) antibody fragments have been isolated from the library of the present invention using phage display technology and an antibody serving as antigen. Such anti-Id antibody fragments have great potential in both evoking the immune system responses to pathological antigens and in vaccine development.

Single Chain Fv-Yst9.1 (Anti-Brucella Antibody)

The above-described naïve llama phage display library was panned against Yst9.1 scFv immobilized on micro-titer plates. A very high enrichment was observed in the case of anti-Brucella carbohydrate (Yst9.1 scFv), as all the 60 selected clones showed strong binding in phage ELISA to Yst9.1 scFv but no binding to the BSA control. Sequencing revealed 17 different sdAbs, some of which, were related to each other (Table 2). For example, Bruc.B3, Bruc.B10 and Bruc.C7.3 have the same CDR3. As another example, Bruc.C7.2, Bruc.D10 and Bruc.E6 have the same CDR3 in addition to the first two, which share the same CDR2. These common sequences were encoded by identical nucleotides raising the possibility that divergent sdAbs may have arisen as a result of PCR cross-over in vitro. Interestingly, the interface amino acids are generally Gly44, Leu45 and Trp47, typical of human/murine VH domain. In addition, none of the isolated sdAbs have any cysteine in CDR1, 2, or 3.

Table 2 also shows the identity of amino acids at positions 37, 44, 45 and 47 of the VL interface of $V_HH$ domain. Interestingly, all sdAbs shown in the table have VL

TABLE 2

CDR/H1 sequences of dAbs which were isolated by panning the llama library against Yst9.1 scFv. The $V_L$ interface residues at positions 37, 44, 45 and 47 are also included.

| sdAb | 37 | 44 | 45 | 47 | CDR1/H1 | CDR2 | | CDR3 | |
|---|---|---|---|---|---|---|---|---|---|
| Bruc.B3 | V | G | L | W | GFTFSSSYAMS | SEQ ID No: 85 | GIEGGGGITRYADSVKG | SEQ ID NO: 119 | AHGGYGAFGS |
| Bruc.B10 | V | G | L | W | GFTFSSYYMS | SEQ ID No: 86 | TIKPGGGSTYYADSVKG | SEQ ID NO: 120 | AHGGYGAFGS |
| Bruc.C7.3 | F | G | F | S | GFTFDEHAIG | SEQ ID No: 87 | TIDIGGGRTYADSVKG | SEQ ID NO: 121 | AHGGYGAFGS |
| Bruc.B8 | V | G | L | W | GFTVSSNHMT | SEQ ID No: 88 | RISSDGRNTYYADSVKG | SEQ ID NO: 122 | YSGGALDA |
| Bruc.D4.4 | V | G | L | W | GFTFSSYHMA | SEQ ID No: 89 | TINPGDGSTYYADSVKG | SEQ ID NO: 123 | YSGGALDA |
| Bruc.C7.2 | F | G | F | Y | GFTFDEHAIG | SEQ ID No: 90 | HIDTGGSTWYAASVKG | SEQ ID NO: 124 | LSQGAMDY |
| Bruc.D10 | V | G | L | Y | GFTFSRHQMS | SEQ ID No: 91 | HIDTGGSTWYAASVKG | SEQ ID NO: 125 | LSQGAMDY |
| Bruc.E6 | V | G | L | W | GFTFRTYYMN | SEQ ID No: 92 | TINIDGSSTYYADSVRG | SEQ ID NO: 126 | LSQGAMDY |
| Bruc.E3.1 | V | G | L | W | GFIFSSYAMS | SEQ ID No: 93 | GINSFGGSKYYADSVKG | SEQ ID NO: 127 | IDRERAFTS |
| Bruc.E7.3 | V | G | F | W | GFIFSSYAMS | SEQ ID No: 94 | GINSFGGSKYYADSVKG | SEQ ID NO: 128 | IDWERAFTS |
| Bruc.C6 | V | G | L | W | GFTFSTYAMT | SEQ ID No: 95 | TINTSGRGTYYADSVKG | SEQ ID NO: 129 | QGYAGSYDY |
| Bruc.C5 | V | G | P | W | GFTFSSYAMS | SEQ ID No: 96 | AINSGGGTSYADSVKG | SEQ ID NO: 130 | LGVPGTFDY |
| Bruc.B7.1 | V | G | L | Y | GFTFSRHQMS | SEQ ID No: 97 | HIDTGGGSTWYAASVKG | SEQ ID NO: 131 | TNRGIFDY |
| Bruc.B7.1A | V | G | P | W | GFTFESRYAMS | SEQ ID No: 98 | DINSGGDSTRNADSVKG | SEQ ID NO: 132 | TPGSSGVYEY |
| Bruc.D6 | V | G | L | W | GFTFSGYAMS | SEQ ID No: 99 | SINSGGGSTYYADSVKG | SEQ ID NO: 133 | TQTGSHDY |
| Bruc.D5 | L | G | F | W | GFAFSNVRMT | SEQ ID No: 100 | RINSIGDRISYADSVKG | SEQ ID NO: 134 | QVGTAYDY |
| Bruc.F7 | V | G | P | W | GFTFSRYAMS | SEQ ID No: 101 | DINSGGDSTRNADSVKG | SEQ ID NO: 135 | RRGSSGVYEY | interface residues which are typical of murine or human VHs. For example, half of the sdAbs have Val37, Gly44, Leu45 and Trp47, which are highly conserved in murine and human VH. In addition, all sdAbs have Val37 and Gly44, and majority has Leu45 and Trp47. Six, three and one sdAbs are characterized by the presence of Phe45 or Pro45, Tyr45 and Ser45, respectively. It is interesting to note that the presence of the same VL interface residues in the conventional antibodies would render the isolated VH highly hydrophobic, resulting in their aggregation, which is not observed for llama antibodies.

With the presence of "human residues" at positions 37, 44, 45 and 47, the entire sequences of the Yst9.1-specific sdAbs are very homologous to human VH3 family sequences. A comparison of a consensus VH3 family sequence and the Yst9.1-specific sdAbs reveals amino acid differences at only five positions (Table 3). One of the five differences, the position 83 difference (Lys in the Yst9.1-specific sdAbs and Arg in the human consensus sequence) is conservative. Spatially, residues 6 and 108 are close and are located in the first and last (ninth) β-strands, respectively. The other three residues are positioned in non-CDR loops. Incorporation of some of these residues into an otherwise insoluble human VH has rendered the domain soluble (unpublished results).

TABLE 3

Amino acid differences between a human VH3 family concensus sequence and the Yst9.1 binders listed in Table 2. Amino Acid positions are indicated in Kabat Numbers.

| Amino acid position | 6 | 74 | 83 | 84 | 108 |
|---|---|---|---|---|---|
| $V_H H$ | Ala | Ala | Lys | Pro | Gln |
| Human VH3 family | Glu | Ser | Arg | Ala | Leu |

Binding Studies

Figure 5:
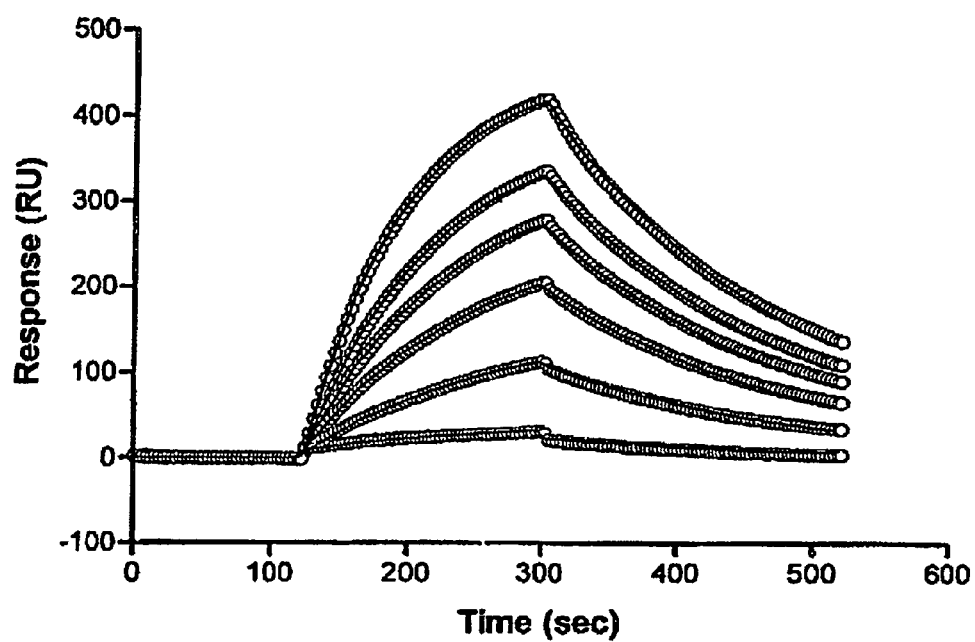
FIG. 5 is a graph showing global fitting to 1:1 interaction model of the binding of Yst9.1 scFv to immobilized Bruc.C6 sdAb fragment at 20, 100, 200, 300, 400, and 600 nM. Open circle lines represent experimental data points, whereas solid lines represent the fit.

One of the anti-Yst 9.1 scFv sdAbs, Bruc.C6, was shown to be specific for its antigen by BIACORE analysis, as it bound to Yst 9.1 scFv (FIG. 5). The kinetic rate constants, $k_a$ and $k_d$, obtained by the global fitting of the binding data, are shown in Table 5. The calculated $K_d$ in this case is 380 nM (Table 5).

TABLE 5

Kinetic and equilibrium constants for the binding of Bruc.C6 to Yst9.1 ScFv and of TNG.P1779 to biotinylated peptide p1779. The values were determined from the retrospective sensograms and Scatchard plots in FIGS. 5, 6 and 7. ND = not determined.

| | $k_a$ (M$^{-1}$s$^{-1}$) | $k_d$ (s$^{-1}$) | $K_d$ (M) ($k_d/k_a$) | $K_d$ (M) (Scatchard plot) |
|---|---|---|---|---|
| Bruc.C6 | 1.4 × 10$^4$ | 5.5 × 10$^{-3}$ | 3.8 × 10$^{-7}$ | ND |
| TNG.P1779 | ND | ND | ND | 1.1 × 10$^{-5}$ |

Selection Against Peptide Antigens

These selection studies were carried out against peptides derived from granulin A and the parathyroid hormone (PTH).

A. Granulin A-Derived Peptides

Proteins of granulin/epithelin family are thought to play a role in inflammation, wound repair, tissue modeling and regulating enzyme activity (Vranken et al., *J. Pept Res.*, 590-597 (1999); Hrabal et al., *Nat Struct Biol.*, 752 (1996)). They are implicated as potential co-factors for HIV Tat protein and in modulating the growth of human epidermal carcinoma cells, and inhibition of their expression is known to inhibit the tumorigenecity of certain cells. The granulin motif has been found throughout the animal kingdom, in fish and insects, and encoded in the genome of a nematode worm. The motif consists of a parallel stacks of beta-hairpins pinned together by disulfide bonds. The structural sub-domain of granulin containing the first two beta-hairpin and spanning the first N-terminal 30 amino acids is also shared by growth factor proteins such as epidermal growth factors, transforming growth factor (TGF)-alpha, as well as the epithelial cell-specific TGF (TGF-e) which modulates the growth of human epidermal carcinoma cells. These growth factors interact with their receptors through their N-terminal beta-hairpin sub-domain and it is believed that epithelin/granulin family of proteins exert their growth modulating effect through the same sub-domain, by interacting with similar receptors. There have been continuous efforts in engineering stable sub-domains as possible drug candidates, with the aim of targeting specific proteins in vivo. The methodology has involved a rational amino acid substitution followed by assessing the effect of substitution on the stability of the sub-domain by NMR studies.

Solution structure of a 30-residue N-terminal sub-domain derived from carp granulin-1 has shown that the fragment forms two beta-hairpins similar to the one in the native protein. Unlike the carp granulin-1 sub-domain, the human counterpart (Tolkatchev et al., *Biochemistry*, 2878-2886 (2000); see also peptide p1779 in Table 6) was not stable outside the context of the native protein and a Q20P substitution (p1781) only slightly improved its stability. A substituted version incorporating D1V, K3H, S9I and Q20P, however, showed a well-folded stack of two beta-hairpins as in the carp granulin-1.

As an alternative and complement to NMR studies, antibodies can be used to probe the structural changes caused by amino acid substitution. The changes in the stability of a sub-domains brought about by amino acid substitutions may be manifested as changes in its affinity for an antibody probe compared to the wild type. Using peptides p1779, p1780 and p1781 shown in Table 6 as a model system it was demonstrated that a sdAb isolated from the llama sdAbs phage display library by panning against p1779 may serve as a structural probe. The sdAb binds to the p1779 peptide with a $K_d$ of 10 μM, but shows no binding to the substituted versions of the peptide (peptides p1780 and p1781), which are known to have structures different from p1779. Other than serving as structural probes, such sdAbs can be used, for example, to interfere with granulin binding in pathways leading to cancer cell growth or HIV progression.

TABLE 6

Sequences of the human granulinA-derived peptide p1779 and its substituted versions p1780 and p1781. For panning experiments the peptides were labelled at the N-terminal through a (Gly)$_4$ linker.

| Peptide | Sequence | |
|---|---|---|
| p1779 | DVKCDMEVSCPDGYTCSRLQSGAWGCSPFT | SEQ ID No: 202 |
| p1780 | VVHCDMEVICPDGYTCSRLPSGAWGCSPFT | SEQ ID No: 203 |
| P1781 | DVKCDMEVSCPDGYTCSRLPSGAWGCSPFT | SEQ ID No: 204 |

Human Granulin A-Derived Peptides

Solution panning was performed against human granulin A-derived peptide, p1779, and its substituted versions, p1780 and p1781 (Table 6). After four rounds of panning against p1779, phage sdAbs from all 48 clones tested were shown to bind to the target antigen. In the case of p1781, only eight binders (four different sequences, Table 4) were identified. No binder was identified for p1780 even after fifth round and performing the panning experiment two more times under different conditions.

Figure 6:
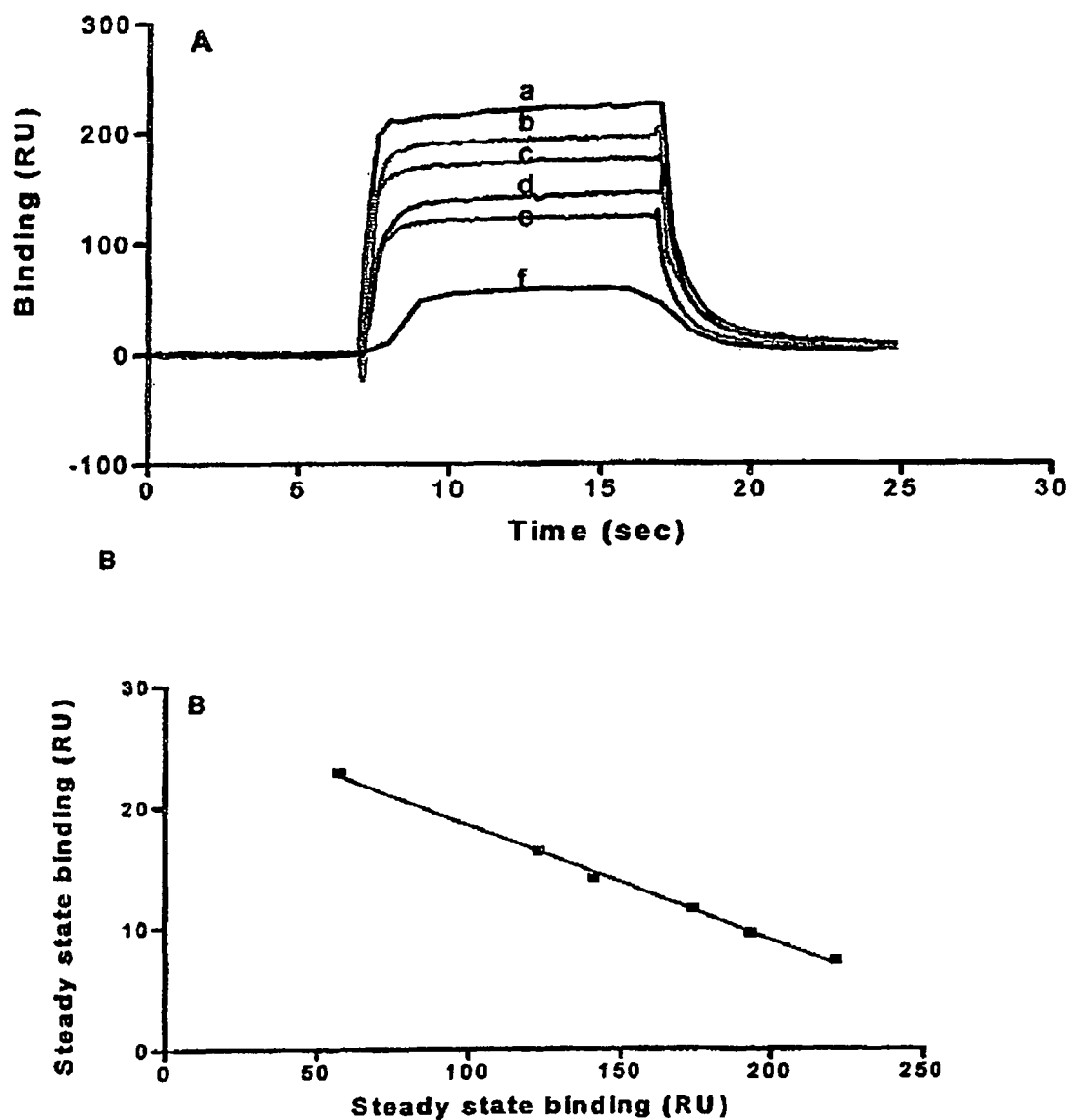
FIG. 6 is a graph showing overlays of sensograms (A) and the Scatchard plot derived therefrom (B) for the binding of TNG.p1779 sdAb fragment (2.5 (f), 7.5 (e), 10 (d), 15 (c), 20 (b) and 30 (a) μM) to captured biotinylated p1779 peptide.

Sequencing of twenty-one p1779-specific sdAb genes identified one fragment, namely, TNG.P1779, which was further expressed for detailed binding studies by BIACORE. In agreement with the phage ELISA results, TNG.P1779 was shown to be active by BIACORE analysis in which biotinylated p1779 was captured on a SA-coated CM5 sensor chip (FIG. 6, part A). No binding was detected to the reference surfaces on which a similar amount of p1780 or p1781 had been captured (data not shown). A Scatchard plot of the binding data gave a $K_d$ of $1.1 \times 10^{-5}$ M (Table 5). These results demonstrate that the TNG.P1779 behaves like a structural probe, sensing the structural changes, which occur in p1780 or p1781 as a result of amino acid substitutions.

B. Parathyroid Hormone-Derived Peptide

Parathyroid hormone (PTH) is the major regulator of serum calcium levels and its use for the treatment of bone loss due to osteoporosis has been postulated. Osteoporosis, which is characterized by bone loss, strikes at any age, affects both men and women, although women with higher frequency, and can results in

TABLE 4

CDR/H1 sequences of dAbs which were isolated by panning the llama library against granulin A-derived peptides p1779 and p1781 (A) and PTH peptides (B). The V_L interface residues 44, 45 and 47 are also included.

| sdAb | 44 | 45 | 47 | CDR1/H1 | | CDR2 | | CDR3 | |
|---|---|---|---|---|---|---|---|---|---|
| (A) | | | | | | | | | |
| TNG.P1779 | Q | R | L | GSRRSFNVMG | SEQ ID No: 136 | TITVGDTTSYAEAVKG | SEQ ID No: 158 | EEMLGVRQNNY | SEQ ID No: 180 |
| TNG.P1781-1 | E | R | L | GDTFSINAYG | SEQ ID No: 137 | AISRGRTNTFVADSVKG | SEQ ID No: 159 | GEY | SEQ ID No: 181 |
| TNG.P1781-2 | G | L | W | GPTFRDYWMY | SEQ ID No: 138 | SIYDGSRTAYAASVKG | SEQ ID No: 160 | MLLGPGAPGYDY | SEQ ID No: 182 |
| TNG.P1781-3 | Q | R | L | GITFSEKHMA | SEQ ID No: 139 | VITRGGTTNYGDSVKG | SEQ ID No: 161 | DFYGLGFDY | SEQ ID No: 183 |
| TNG.P1781-4 | E | R | F | ERTFNSYAAA | SEQ ID No: 140 | GITKNGVTYYAPSVTG | SEQ ID No: 162 | APKYEGVSDTSSDYNY | SEQ ID No: 184 |
| (B) | | | | | | | | | |
| TNG.PTH1 | E | R | F | GRTFSSYGMG | SEQ ID No: 141 | AMRESGADTHYADFVRG | SEQ ID No: 163 | LDITTAASY | SEQ ID No: 185 |
| TNG.PTH2 | E | R | F | GRTFSSYGMG | SEQ ID No: 142 | AMRESGADTHYADFVRG | SEQ ID No: 164 | TINGAAR | SEQ ID No: 186 |
| TNG.PTH4 | K | R | L | GTSSGINAMV | SEQ ID No: 143 | TITNSGKTDYAASAKG | SEQ ID No: 165 | TINGAAR | SEQ ID No: 187 |
| TNG.PTH5 | E | R | F | GRTFSSYSMA | SEQ ID No: 144 | AINWRSSVTAYADSVKG | SEQ ID No: 166 | EALPGTYGLDY | SEQ ID No: 188 |
| TNG.PTH7 | E | R | L | VSTFSIGAIG | SEQ ID No: 145 | GISGGGSTYYTDSVKG | SEQ ID No: 167 | ILAGGLLAF | SEQ ID No: 189 |
| TNG.PTH8 | Q | R | L | GSTFSGNDIG | SEQ ID No: 146 | VISDGGYTSYATSVKG | SEQ ID No: 168 | GGSSGTF | SEQ ID No: 190 |
| TNG.PTH9 | E | R | F | GRTFSSYGMG | SEQ ID No: 147 | AISWGAGTPYYADSVKG | SEQ ID No: 169 | TINGAAR | SEQ ID No: 191 |
| TNG.PTH10 | E | R | I | GRTFSDIAMA | SEQ ID No: 148 | AIDWNGGTTYYTTFVKG | SEQ ID No: 170 | LDITTAASY | SEQ ID No: 192 |
| TNG.PTH11 | E | R | F | GQTLNTYVMG | SEQ ID No: 149 | AINWRDTSTYYQDSVKG | SEQ ID No: 171 | TINGAAR | SEQ ID No: 193 |
| TNG.PTH12 | E | R | F | GPTSITYGMA | SEQ ID No: 150 | AVTPSGGAAAVADSVKG | SEQ ID No: 172 | GTELAPKTATGA | SEQ ID No: 194 |
| TNG.PTH14 | E | R | F | GGDVSTYAMV | SEQ ID No: 151 | LLSRSGRTTNYADSVKG | SEQ ID No: 173 | GSN | SEQ ID No: 195 |
| TNG.PTH15 | Q | R | L | GRTFGSYTMG | SEQ ID No: 152 | RINSAGRTMYADSVKG | SEQ ID No: 174 | GTVLSVATGPYGY | SEQ ID No: 196 |
| TNG.PTH18 | E | R | F | GRTFSSYGMG | SEQ ID No: 153 | SINWRGSSTYYADSVKG | SEQ ID No: 175 | WGAGEDEDY | SEQ ID No: 197 |
| TNG.PTH22 | E | R | L | GSLSRITVMG | SEQ ID No: 154 | IITSSGGTDYADSVKG | SEQ ID No: 176 | KSRDSAGLSWDY | SEQ ID No: 198 |
| TNG.PTH23 | Q | R | V | GSISSFDAMA | SEQ ID No: 155 | IITSGGATNYADSVKG | SEQ ID No: 177 | LVASTVTSSVS | SEQ ID No: 199 |
| TNG.PTH50 | E | R | F | GRPFSSFAMG | SEQ ID No: 156 | AISASGGETYYTGSLKG | SEQ ID No: 178 | TINGAAR | SEQ ID No: 200 |
| TNG.PTH61 | E | R | F | GRTFSSYHMG | SEQ ID No: 157 | AINWSGDTTYYEASVKG | SEQ ID No: 179 | QTRPRPYGTSRAEGDYGY | SEQ ID No: 201 | hospitalization, disability and death (Morley et al., Current Medicinal Chemistry, 6, 1095-1106 (1999); Whitfield et al., *Drugs & Aging*, 15(2), 117-129 (1999)). Most of the available drugs slow down or stop further bone loss, but have no bone growth-stimulating effects, hence are not capable of replacing the lost bones.

The bone-building action of the parathyroid hormone (PTH) and its implications for the treatment of osteoporosis has been recently reviewed (Whitfield et al., supra). PTH is expressed as a 115 amino acid precursor and secreted as a 84-residue peptide, but its bone growth-stimulating effects have been related to its N-terminal 34-residues peptide and shown to be the case in human trials. More recently, mutated and cyclized PTH peptide analogues have been shown to be more potent bone growth stimulators in in vitro studies (Morley et al., *Expert Opin. Therap. Pat.*, 8, 30-37 (1998)). These analogues, which have been patented, show great promise as drugs for the treatment of osteoporosis and are currently at the clinical trial stage. However, to meet the regulatory requirements, the pharmacokinetics of these drugs needs to be monitored following their administration to human subjects. This can be achieved by obtaining reagents, such as antibodies, capable of specifically recognizing the PTH analogues present in biological samples. Within the past two years, attempts were made to raise such antibodies by conventional hybridoma technology, but no success was reported. In the present study, a number of sdAbs specific for the PTH peptide analogues PTH1 and PTH2 (Table 7) have been isolated from the phage display library of sdAb fragments of heavy chain antibodies derived from a naïve library of llama antibodies.

TABLE 7

Sequences of PTH1 and PTH2 peptides corresponding to N-terminal residues 17-31 (PTH1) and 1-31 (PTH2) of the human PTH. Compared to the human PTH, these analogs have a substitution at positions 37(K37L) and a β-lactam bond connecting the side chains of $^{22}$E and $^{26}$K.

| Peptide | Sequence | | |
|---|---|---|---|
| PTH1 | $^{17}$SMERVEWLRKLLQDV$^{31}$ | SEQ ID No: | 205 |
| PTH2 | $^{1}$SVSEIQLMHNLGKHLNSMERVEWLRKLLQDV$^{31}$ | SEQ ID No: | 206 |

Human PTH-Derived Peptides

Figure 7:
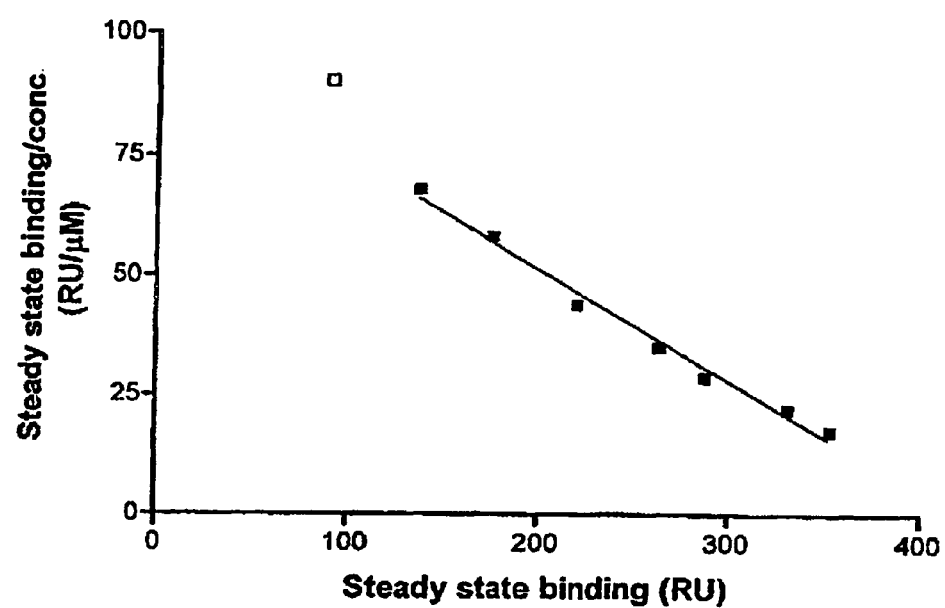
FIG. 7 is a graph showing the Scatchard plot derived from sensograms for the binding of TNG.PTH50 sdAb fragment to captured biotinylated PTH2 peptide.

Panning against PTH1 resulted in the identification of thirteen different sdAbs, all of which bound to PTH1 in a phage ELISA (Table 4, TNG.PTH1 through TNG.PTH18). Four binders were identified for PTH2 (Table 4, TNG.PTH22, TNG.PTH23, TNG.PTH50 and TNG.PTH61). The binding sdAbs were expressed and purified in large quantities. The expression level was high and for one particular sdAb it exceeded 200 mg of protein per liter of bacterial culture. Three sdAbs were characterized in more details by surface plasmon resonance and shown to bind to their target antigens (Table 8). FIG. 7 shows the binding profile for TNG.PTH50 which was isolated by panning against PTH2. The calculated $K_d$ for TNG.PTH50 is $4.3 \times 10^{-6}$ which is shown in Table 8.

TABLE 8

Equilibrium constants for the binding of TNG.PTH22, TNG.PTH23 and TNG.PTH50 to biotinylated PTH2. The values were determined from the respective sensograms and Scatchard plots, as shown in FIG. 7 for TNG.PTH50.

| sdAb | $K_d$ (M) |
|---|---|
| TNG.PTH22 | $1.4 \times 10^{-5}$ |
| TNG.PTH23 | $5.7 \times 10^{-5}$ |
| TNG.PTH50 | $4.3 \times 10^{-6}$ |

Experimental

All reagents were chemical grade purchased from various companies. Unless stated otherwise, the media were prepared as described (Sambrook et al., Molecular Cloning: A Laboratory Manual, 2nd ed., Cold Spring Harbour Laboratory, Cold Spring Harbour, N.Y. (1989)). Phosphate-buffered saline (PBS) was prepared as described (Sambrook et al., supra). Induction medium was the same as Terrific Broth except that it contained no salts. Agarose top was prepared by combining the following reagents in a total volume of 1 liter: 10 g Bacto-tryptone, 5 g yeast extract, 10 g NaCl, 1 g MgCl2.6H2O, and 7 g agarose. The mixture was autoclaved and stored solid at room temperature. The oligonucleotides were synthesized using the Applied Biosystems 394 DNA/RNA synthesizer. DNA sequencing was performed by the dideoxy method [Sanger, F., Nicklen, S., and Coulson, A. R., 1992]) using the AmpliTaq DNA Polymerase FS kit and 373A DNA Sequencer Stretch (PE Applied Biosystems, Mississauga, ON, Canada). The host bacteria used for cloning was TG1: supE hsd5 thi (lac-proAB) F' [traD36 proAB$^+$ lacI$^q$ lacZM15]. All the cloning steps were performed as described (Sambrook et al., supra). The vector fd-tet was purchased from American Type Culture Collection (Manassas, Va.) and engineered such that it contained ApaI and NotI restriction sites immediately following the gIIIp leader sequence codons (Simon J. Foote, personal communications).

Construction of Naive llama sdAb Library

Total RNA was isolated from the leukocytes of freshly-drawn heparinized blood of a male Llama (Lama glama) using QIAamp RNA Blood Mini™ kit (QIAGEN, Mississauga, ON, Canada) and following the recommended protocol. The concentration of RNA was calculated by measuring the A260 value and assuming 1 A260=40 µg/ml. Reverse transcription-polymerase chain reaction (RT-PCR) was performed on a total of 5.3 µg RNA using the HotStarTaq Polymerase™ kit (QIAGEN). The primers used included a CH2-specific primer, LlamaFOR, 5'(CGCCATCMGGTACCAGTTGA)3' [SEQ ID No: 207] and LlamaBACK primer, 5'(GATGTGCAGCTGCAG-GCGTCTGGRGGAGG)3' [SEQ ID No: 208], which anneals to the 5' flanking region of VH genes. Amplified product of approximately 600 base pair was purified from the agarose gel using QIAquick Gel Extraction™ kit (QIAGEN) and subjected to a second round of PCR using the primers LlamaApaII, 5'(CATGACCACAGTGCACAG-GAKGTSCAGCT)3' [SEQ ID No: 209] and LlamaNotI, 5'(CGATTCTGCGGCCGCTGAGGAGACGGTGACCTG) 3' [SEQ ID No: 210]. The PCR mixture contained 10 pmol/µl each of the two primers, 1× buffer (Perkin Elmer), 200 µM each of the four dNTPs and 0.05 unit/µl AmpliTaq™ DNA polymerase (Perkin Elmer). PCR protocol consisted of an initial denaturation step at 95° C. for 15 min followed by 35 cycles of 94° C. for 30 sec, 45° C. for 30 sec, and 72° C. for 1 min, and a final extension step at 72° C. for 10 min. The primers were complimentary to the 5' and 3' ends of the amplified product and incorporated ApaII and NotI restriction sites (underlined) at the end of VH genes. The amplified products were purified using QIAquick PCR Purification Kit™ (QIAGEN), cut sequentially with ApaII and NotI restriction endonucleases, purified again, ligated to the ApaII/NotI-treated fd-tet phage vector and desalted using the above kit. Electrocompetent TG1 cells were prepared [Tung, W. L. and Chow, K. C., 1995]) and 1.5 µg of the ligated product was mixed with 40 µl of competent *E. coli* strain TG1 and the cells were transformed by electroporation using the BIO-RAD Gene Pulser™ according to the manufacturer's instructions. The transformed cells were immediately transferred into 1 ml of SOC medium and split into 3 sterile tubes containing 3 ml of 50° C. agarose top, vortexed immediately, poured onto pre-warmed 2×YT petri dishes, and incubated at 37° C. overnight. The phage particles were eluted by adding five ml of sterile PBS to the plates gently shaked at 4° C. for 3 hr. The phage-containing PBS was collected, the plates were rinsed with an additional 5 ml PBS and the two supernatants were combined in a centrifuge bottle. The contents were centrifuged at 6000 g for 15 min at 4° C., the supernatant was decanted into a sterile centrifuge bottle and the phage was purified as described (Harrison et al., supra). At the end of the purification, the phage pellet was dissolved in 20 ml of sterile PBS and stored in liquid nitrogen in 100 µl aliquots.

To determine the size of the library, immediately following the transformation and after the addition of the SOC medium, a small aliquot of the electroporated cells was serially diluted in exponentially growing TG1 cells. 200 µl of the diluted cells was mixed with 3 ml of 50° C. agarose top and immediately poured onto 2×YT plates pre-warmed to 37° C. Plates were incubated overnight at 37° C. and the number of plaques was used to determine the size of the library.

Panning

Panning was performed using the Nunc-Immuno MaxiSorp™ 8-well strips (Nunc). Briefly, the wells were coated overnight by adding 150 µl of 100 µg/ml antigen in PBS. In the morning, the wells were rinsed three times with PBS and subsequently blocked with 400 µl PBS-2% (w/v) skim milk (2% MPBS) at 37° C. for 2 hr. The wells were rinsed as above and 1012 transducing units phage in 2% MPBS were added.

The mixture was incubated at room temperature for 1.5 hr after which the unbound phage in the supernatant was removed. The wells were rinsed 10 times with PBS-0.1% (v/v) Tween 20 and then 10 times with PBS to remove the detergent. The bound phage was eluted by adding freshly prepared 200 µl 100 mM triethylamine, pipetting the content of the well up and down several times and incubating the mixture at room temperature for 10 min. The eluted phage was transferred to a tube containing 100 µl 1 M Tris-HCl, pH 7.4 and vortexed to neutralize the triethylamine. Following this, 10 ml of exponentially growing TG1 culture was infected with 150 µl eluted phage by incubating the mixture at 37° C. for 30 min. Serial dilutions of the infected cells were used to determine the titer of the eluted phage as described in the previous section. The remainder of the infected cells was spun down and then resuspended in 900 µl 2×YT. The cells were mixed in 300 µl aliquots with 3 ml agarose top and the phage propagated on the plates overnight at 37° C. In the morning the phage was purified, the titer was determined, and a total of $10^{11}$ transducing units phage were used for further rounds of selection.

Solution Panning

Solution panning was performed using SA-PMP (1 mg/ml) obtained from Promega (Madison, Wis.). To maintain SA-PMP in solution during the panning process, the reaction tubes were flicked frequently during the incubation period. Briefly, for each target antigen 2×100 µl SA-PMPs was first dispersed by gently flicking the bottom of the tubes, and then captured at the side of the tube in a magnetic stand (approximately 30 sec.) followed by careful removal of the supernatant. SA-PMPs were re-suspended in 100 µl 1×PBS, re-captured and the supernatant was removed. This washing process was repeated three times. To remove any possible streptavidin binders from the phage library the phage particles were pre-incubated with SA-PMP in 2% MPBS for 1 hr at room temperature and the magnetic beads were captured. To form the phage-antigen complex, $10^{12}$ t.u. phage ($10^{11}$ t.u. for further rounds) in the supernatant was incubated in 2% MPBS containing 20 mg/ml BSA, 0.05% Tn20 and 1 µg/ml biotinylated antigen in a total volume of 150 µl for 1 hr at room temperature. In a second tube 100 µl of the washed SA-PMP was blocked in 400 µl 2% MPBS at 37° C. for 2 hr. The supernatant was discarded and the phage-biotinylated antigen complex solution from the first tube was added to the blocked SA-PMP at room temperature for 30 min. The supernatant was removed and the complex-bound SA-PMPs were washed twice with 100 µl PBS and then once with 100 µl 2% MPBS containing 0.05% Tn 20; this sequence of washes was repeated another three times and then finally SA-PMPs were washed twice with PBS. The bound phage was eluted by adding 200 µl of 100 mM freshly prepared triethylamine and standing at room temperature for 10 min. Phage elution, propagation, titering and purification were performed as described for solid phase panning. Depending on the antigen for the final third and fourth rounds the procedure preceding the elution step was modified as described below. Following the initial washing step, 100 µl SA-PMPs were blocked followed by removal of supernatant and subsequent incubation of SA-PMPs with 100 µl of 5 µg/ml biotinylated antigens in 2% MPBS at room temperature for 30 min. The antigen-bound SA-PMPs were washed 5 times with 0.5% MPBS and then incubated with phage in 2% MPBS at room temperature for 1.5 hr in a total volume of 100 µl. The supernatant was removed and the phage bound SA-PMPs were washed eight times with 0.5% MPBS and two times with PBS before proceeding with the elution step.

Phage Enzyme-Linked Immunosorbent Assay (Phage ELISA)

Individual phage-infected TG1 colonies were used to inoculate 200 µl of LB in sterile 96-well plates. The cells were grown overnight at 100 rpm and 37° C. In the morning, the plates were spun down in a bench top centrifuge, and the sdAb phage-containing supernatant was used for phage ELISA as described below. Briefly, Nunc-Immuno MaxiSorp™ plates (Nunc) were coated overnight at 4° C. with 150 µl of 10 µg/ml of target antigen or control proteins in PBS. The contents were removed and the plates were tapped on a paper towel to remove any liquid remaining in the wells. The wells were blocked by adding 300 µl of PBS-2% (w/v) skim milk (2% MPBS) and incubating for 2 hr at 37° C. The contents of the wells were emptied as before, 100 µl of sdAb phage supernatant in 2% MPBS was added, and the wells were incubated at room temperature for 1.5 hr. For biotinylated antigen, the plates were pre-coated with 5 µg/ml streptavidin overnight followed by blocking. The wells were then coated with the target antigen by incubating plates with 150 µl of 1 µg/ml biotinylated antigen at room temperature for 30 min. The wells were washed 5× with PBS-0.05% (v/v) Tween 20 (PBST) and then incubated with phage. For control experiments no coating with the biotinylated antigen was performed. The contents were emptied again and the wells were washed 5 times with PBST and subsequently blotted on a paper towel to remove any remaining wash buffer. 100 µl of the recommended dilution of HRP/Anti-M13 Monoclonal Conjugate (Amersham Pharmacia Biotech, Montreal, QC, Canada) in 2% MPBS was added and the wells were incubated at room temperature for 1 hr. The wells were washed six times as before and the binding of sdAb to the antigen was detected colorimetrically by adding 100 µl of equal mixtures of TMB Peroxidase Substrate and H2O2 (KPL, Maryland, USA) at room temperature for several min. The reaction was stopped by adding 100 µl of 1 M H3PO4 and the A450 was measured by DYNATECH MR5000 ELISA reader (DYNATECH).

Sub-Cloning and Expression of sdAbs sdAb genes were amplified out of the phage vector by PCR using the primers, VH.Bbs, 5'(TATGAAGACACCAGGCCGATGTGCAGCTGCAGGCG)3' [SEQ ID No: 211], and VH.Bam, 5'(TATGGATCCTGAGGAGACGGTGACCTG)3' [SEQ ID No: 212] which also introduced BbsI and BamHI sites at the ends of the amplified fragments. sdAb genes were subsequently purified, cut sequentially with BbsI and BamHI restriction endonucleases, purified again with QIAquick Gel Extraction™ kit (QIAGEN), and ligated to the BbsI/BamHI-treated pSJF-2 vector. An aliquot of the ligated product was used to transform *E. coli* strain TG1. Transformants were selected on ampicillin plates and the clones harbouring the sdAb genes were identified by PCR and sequencing. For expression, single positive clones were used to inoculate 25 ml of LB containing 100 µg/ml ampicillin and the culture was shaken at 240 rpm at 37° C. overnight. In the morning, the entire overnight culture was used to inoculate 1 liter of M9 medium supplemented with 5 µg/ml vitamin B1, 0.4% casamino acid and 100 µg/ml ampicillin. The culture was shaken at room temperature for 30 hr at 180 rpm and subsequently supplemented with 100 ml of 10× induction medium and 100 µl of 1 M isopropylthio-D-galactoside. The culture was shaken for another 60 hr, the periplasmic fraction was extracted by osmotic shock [Anand, N. N., Dubuc, G., Phipps, J., MacKenzie, C. R., Sadowska, J., Young, N. M., Bundle, D. R., and Narang, S. A., 1991]) and the presence of sdAb in the extract was detected by Western blotting ([MacKenzie, C. R., Sharma, V., Brummell, D., Bilous, D., Dubuc, G., Sadowska, J., Young, N. M., Bundle, D. R., and Narang, S. A., 1994])). The periplasmic fraction was dialyzed extensively in 10 mM HEPES (N-[2-hydroxyethyl]piperazine-N'-[2-ethanesulfonic acid]) buffer pH 7.0, 500 mM NaCl. The presence of the sdAb C-terminal His5 tag allowed a one step protein purification by immobilized metal affinity chromatography using HiTrap Chelating™ column (Phamacia). The 5-ml column was charged with $Ni^{2+}$ by applying 30 ml of a 5 mg/ml NiCl2.6H2O solution and subsequently washed with 15 ml deionized water. Purification was carried out as described (MacKenzie, supra) except that the starting buffer was 10 mM HEPES buffer, 10 mM imidazole, 500 mM NaCl, pH 7.0, and the bound protein was eluted with a 10-500 mM imidazole gradient. The purity of the protein was determined by SDS-PAGE (Laemmeli U.K., in: Proteases and biological control [Reich et al., ed.], Cold Spring Harbour Laboratory, pp. 661-676 (1975)). sdAb preparation was further subjected to gel filtration chromatography using Superdex 75 column (Pharmacia) as described [Deng, S. J., MacKenzie, C. R., Hirama, T., Brousseau, R., Lowary, T. L., Young, N. M., Bundle, D. R., and Narang, S. A., 1995])) and the purified monomer species were used in binding studies by surface plasmon resonance.

Surface Plasmon Resonance Analysis

Binding studies were performed using BIACORE 1000 [Jonsson, U., Fagerstam, L., Ivarsson, B., Johnsson, B., Karlsson, R., Lundh, K., Lofas, S., Persson, B., Roos, H., Ronnberg, I., and et, al, 1991]) available from Biacore Inc., Piscataway, N.J. Binding of the anti-Yst9.1 sdAbs to Yst9.1 scFv was assessed under the same conditions except that in this case sdAb was immobilized (540 RU) and the flow rate was set at 20 µl/min. For PTH binders 186 RU (PTH2) or 70 RU (control peptide) was immobilized and the flow rate was also set at 20 µl/min. Surface regeneration was achieved by washing the sensor chips with HBST buffer. In the case of p1779 binder, sdAb was passed over biotinylated p1779 (520 RU) or p1780 and p1781 control peptides (420 RU) which had been captured on a CM5 sensor chip coated with streptavidin (2260 RU). Kinetic rate constants were determined using BIAevaluation software and fitting to 1:1 interaction model. Affinity constants were calculated from the kinetic rate constants and by Scatchard analysis of equilibrium binding data as described [MacKenzie, C. R., Hirama, T., Deng, S. J., Bundle, D. R., Narang, S. A., and Young, N. M., 1996]*J. Biol. Chem,* 1527-1533 (1996)).

Although various particular embodiments of the present invention have been described hereinbefore for the purpose of illustration, it would be apparent to those skilled in the art that numerous variations may be made thereto without departing from the spirit and scope of the invention, as defined in the appended claims.

What is claimed is:

1. An isolated single domain antibody binding specifically to a preselected antigen comprising a variable heavy domain (VHH or VH) of an antibody, wherein amino acid residues of the VL interface of the variable heavy domain (VHH or VH) are i) Gly at position 44 according to Kabat numbering, Leu at position 45 according to Kabat numbering, and Trp at position 47 according to Kabat numbering, or ii) Gly at position 44 according to Kabat numbering, Leu at position 45 according to Kabat numbering, and Tyr at position 47 according to Kabat numbering, or iii) Gly at position 44 according to Kabat numbering, Phe at position 45 according to Kabat numbering, and Trp at position 47 according to Kabat numbering, or iv) Gly at position 44 according to Kabat numbering, Pro at position 45 according to Kabat numbering, and Trp at position 47 according to Kabat numbering, wherein in the variable heavy domain (VHH or VH), the amino acid at position 6 is Ala, the amino acid at position 74 is Ala, the amino acid at position 83 is Lys, the amino acid at position 84 is Pro, and the amino acid at position 108 is Gln, said positions according to Kabat numbering; and wherein the CDR3 region of the variable heavy domain (VHH or VH) is selected from the group consisting of: AHGGYGAFGS (SEQ ID NO: 119); YSGGALDA (SEQ ID NO: 122); LSQGAMDY (SEQ ID NO: 124); IDRERAFTS (SEQ ID NO: 127); IDWERAFTS (SEQ ID NO: 128); QGYAGSYDY (SEQ ID NO: 129); LGVPGTFDY (SEQ ID NO: 130); TNRGIFDY (SEQ ID NO: 131); TPGSSGVYEY (SEQ ID NO: 132); TQTGSHDY (SEQ ID NO: 133); QVGTAYDY (SEQ ID NO: 134); and RRGSSGVYEY (SEQ ID NO: 135).

2. The isolated single domain antibody according to claim 1, that does not display aggregation tendencies.

3. The isolated single domain antibody according to claim 1, that has a high degree of homology to the human VH3 family of sequences.

4. The isolated single domain antibody according to claim 1, produced in bacteria.

5. The isolated single domain antibody according to claim 4, wherein the bacteria are *E. coli.*

6. The isolated single domain antibody according to claim 1, comprising at least a part of the variable heavy domain ($V_H$H or VH) of an camelid antibody.

7. The isolated single domain antibody according to claim 1, comprising at least a part of the variable heavy domain ($V_H$H or VH) of a llama antibody.

8. The isolated single domain antibody according to claim 1, wherein amino acid residues at positions 44, 45 and 47 according to Kabat numbering are Gly, Leu and Trp, respectively.

9. The isolated single domain antibody according to claim 1, wherein amino acid residues at positions 44, 45 and 47 according to Kabat numbering are Gly, Pro and Trp, respectively.

10. An isolated antigen-binding fragment of an antibody, said fragment binding specifically to a preselected antigen and comprising a variable heavy domain (VHH or VH) of the antibody, wherein amino acid residues of the VL interface of the variable heavy domain (VHH or VH) are
    i) Gly at position 44 according to Kabat numbering, Leu at position 45 according to Kabat numbering, and Trp at position 47 according to Kabat numbering, or
    ii) Gly at position 44 according to Kabat numbering, Leu at position 45 according to Kabat numbering, and Tyr at position 47 according to Kabat numbering, or
    iii) Gly at position 44 according to Kabat numbering, Phe at position 45 according to Kabat numbering, and Trp at position 47 according to Kabat numbering, or
    iv) Gly at position 44 according to Kabat numbering, Pro at position 45 according to Kabat numbering, and Trp at position 47 according to Kabat numbering, wherein in the variable heavy domain (VHH or VH), the amino acid at position 6 is Ala, the amino acid at position 74 is Ala, the amino acid at position 83 is Lys, the amino acid at position 84 is Pro, and the amino acid at position 108 is Gln, said positions according to Kabat numbering; and wherein the CDR3 region of the variable heavy domain (VnH or VH) is selected from the group consisting of: AHGGYGAFGS (SEQ ID NO: 119); YSGGALDA (SEQ ID NO: 122); LSQGAMDY (SEQ ID NO: 124); IDRERAFTS (SEQ ID NO: 127); IDWERAFTS (SEQ ID NO: 128); QGYAGSYDY (SEQ ID NO: 129); LGVPGTFDY (SEQ ID NO: 130); TNRGIFDY (SEQ ID NO: 131); TPGSSGVYEY (SEQ ID NO: 132); TQTGSHDY (SEQ ID NO: 133); QVGTAYDY (SEQ ID NO: 134); and RRGSSGVYEY (SEQ ID NO: 135).

11. An isolated antigen-binding fragment according to claim 10, wherein said fragment comprises a complete variable heavy domain ($V_H$H or VH) of the antibody.

12. An isolated antigen-binding fragment according to claim 11, wherein said fragment consists essentially of the variable heavy domain ($V_H$H or VH) of a camelid antibody.

13. An isolated antigen-binding fragment according to claim 12, wherein the antibody is selected from the antibody repertoire of a non-immunized camelid.

14. An isolated antigen-binding fragment according to claim 13, wherein the complementarity determining regions CDR1/H1, CDR2 and CDR3 of the variable heavy domain ($V_H$H or VH) are essentially free of cysteine residues.

15. An isolated antigen-binding fragment according to claim 14, wherein said fragment has at position 45 according to Kabat numbering an amino acid residue other than cysteine.

16. An isolated antigen-binding fragment according to claim 10, wherein amino acid residues at positions 44, 45 and 47 according to Kabat numbering are Gly, Leu and Trp, respectively.

17. An isolated antigen-binding fragment according to claim 10, wherein amino acid residues at positions 44, 45 and 47 according to Kabat numbering are Gly, Pro and Trp, respectively.

* * * * *